(12) United States Patent
Schwamb et al.

(10) Patent No.: US 11,389,184 B2
(45) Date of Patent: Jul. 19, 2022

(54) SYSTEM AND METHOD FOR CONNECTING AN INSTRUMENT

(71) Applicant: Medtronic Xomed, Inc., Jacksonville, FL (US)

(72) Inventors: Jeffrey M. Schwamb, Saint Marys, GA (US); Samuel Gladstone, Jacksonville, FL (US); Phillip Berman, Jacksonville, FL (US); Ali Mowlai-Ashtiani, Jacksonville, FL (US); John R. Prisco, St. Johns, FL (US); Alana M. Lacy, Chandler, AZ (US)

(73) Assignee: Medtronic Xomed, Inc., Jacksonville, FL (US)

( * ) Notice: Subject to any disclaimer, the term of this patent is extended or adjusted under 35 U.S.C. 154(b) by 506 days.

(21) Appl. No.: 16/055,782

(22) Filed: Aug. 6, 2018

(65) Prior Publication Data

US 2020/0038046 A1 Feb. 6, 2020

(51) Int. Cl.
| | | |
|---|---|---|
| *A61B 17/29* | (2006.01) | |
| *A61B 34/20* | (2016.01) | |
| *A61B 34/30* | (2016.01) | |
| *A61B 17/00* | (2006.01) | |

(52) U.S. Cl.
CPC .......... *A61B 17/2909* (2013.01); *A61B 34/20* (2016.02); *A61B 34/30* (2016.02); *A61B 2017/0046* (2013.01); *A61B 2017/00199* (2013.01); *A61B 2017/00389* (2013.01); *A61B 2017/00398* (2013.01);

(Continued)

(58) Field of Classification Search
CPC .... A61B 17/320016; A61B 2017/0046; A61B 2017/00464; A61B 17/2909; A61B 2018/0091; A61B 2018/00916; A61B 2018/00958; A61B 2018/0231
See application file for complete search history.

(56) References Cited

U.S. PATENT DOCUMENTS

| | | | |
|---|---|---|---|
| 6,474,341 B1 | 11/2002 | Hunter et al. | |
| 7,247,161 B2 * | 7/2007 | Johnston | A61B 17/1679 |
| | | | 606/170 |
| 7,697,972 B2 | 4/2010 | Verard et al. | |

(Continued)

FOREIGN PATENT DOCUMENTS

| | | |
|---|---|---|
| WO | 03013372 A2 | 2/2003 |
| WO | 03079911 A1 | 10/2003 |

(Continued)

OTHER PUBLICATIONS

International Search Report and Written Opinion for Application No. PCT/US2019/045157, dated Nov. 22, 2019.

(Continued)

*Primary Examiner* — Wade Miles
*Assistant Examiner* — Mohammed S Adam
(74) *Attorney, Agent, or Firm* — Harness, Dickey & Pierce, P.L.C.

(57) ABSTRACT

Disclosed is an instrument assembly usable in a procedure. The instrument includes a connection for a working portion and to a tool handle. The assembly includes a method and system for interconnection and/or identification of the working portion and the handle. The instrument may also include various trackable features to allow for a navigated procedure.

23 Claims, 8 Drawing Sheets

(52) U.S. Cl.
CPC ............... *A61B 2017/00477* (2013.01); *A61B 2017/2901* (2013.01); *A61B 2017/292* (2013.01); *A61B 2017/2948* (2013.01)

(56) References Cited

U.S. PATENT DOCUMENTS

| | | | |
|---|---|---|---|
| RE44,385 E | 7/2013 | Johnson | |
| 8,644,907 B2 | 2/2014 | Hartmann et al. | |
| 8,842,893 B2 | 9/2014 | Teichman et al. | |
| 9,211,163 B1 | 12/2015 | Jaramaz et al. | |
| 9,867,674 B2 | 1/2018 | Hartmann et al. | |
| 2003/0165794 A1 | 9/2003 | Matoba | |
| 2004/0199072 A1 | 10/2004 | Sprouse et al. | |
| 2013/0197552 A1 | 8/2013 | O'Brien, II | |
| 2015/0133922 A1 | 5/2015 | Edwards et al. | |
| 2015/0272608 A1 | 10/2015 | Gladstone | |
| 2016/0120609 A1 | 5/2016 | Jacobsen et al. | |
| 2016/0310218 A1 | 10/2016 | Ruckel et al. | |
| 2019/0104932 A1* | 4/2019 | Truckai | A61B 1/05 |

FOREIGN PATENT DOCUMENTS

| | | |
|---|---|---|
| WO | 2017/052704 A2 | 3/2017 |
| WO | 2017/163226 A1 | 9/2017 |

OTHER PUBLICATIONS

International Search Report and Written Opinion for Application No. PCT/US2019/045165, dated Nov. 5, 2019.
International Search Report and Written Opinion regarding International Application No. PCT/US2019/045151, dated Oct. 14, 2019.
NTAG I2C Explorer Kit Contents, https://nxp-rfid.com/products/ntag/ntag-i2c-explorer-kit-contents/, 8 pgs., 2018.
NTAG I2C Explorer Kit user's manual, 55 pgs., 2014.

* cited by examiner

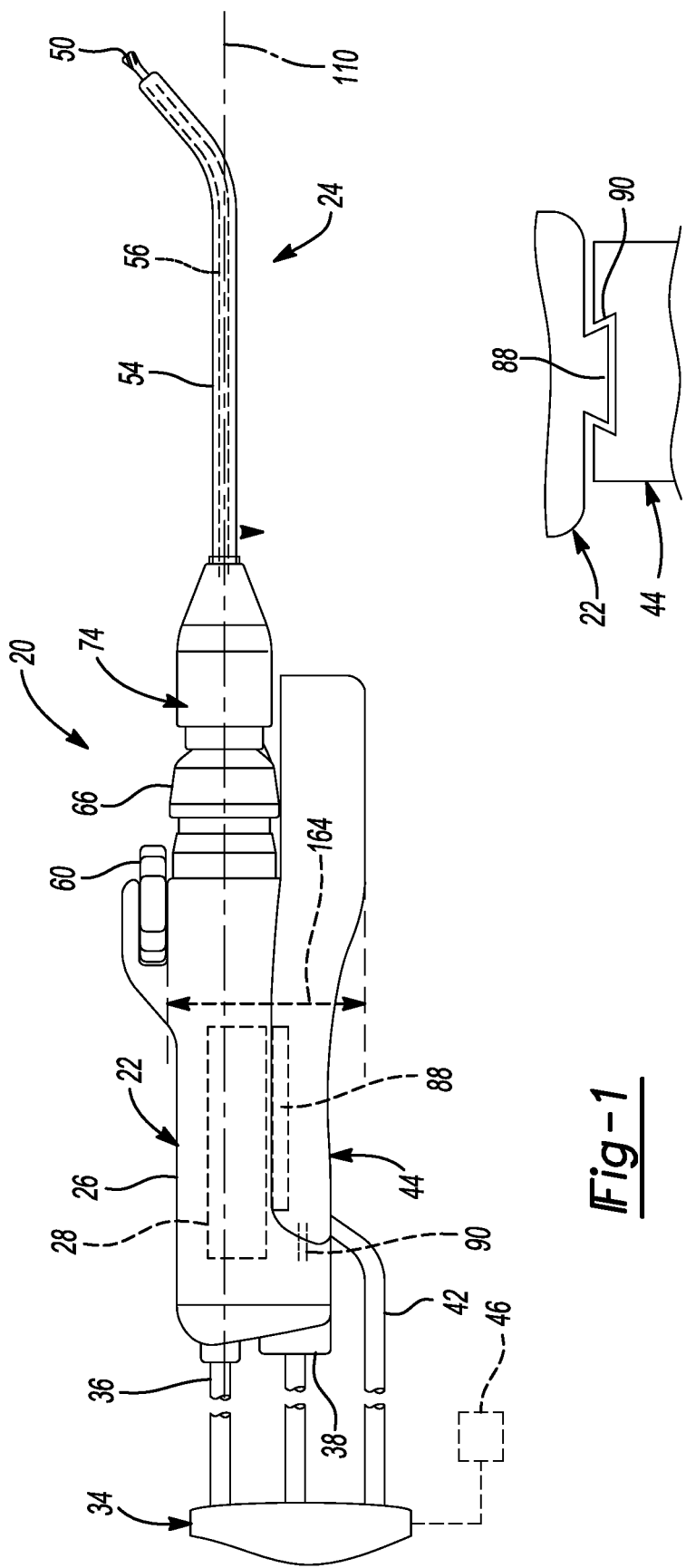
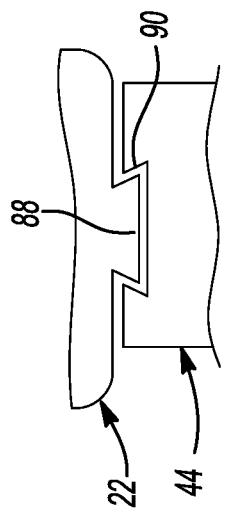

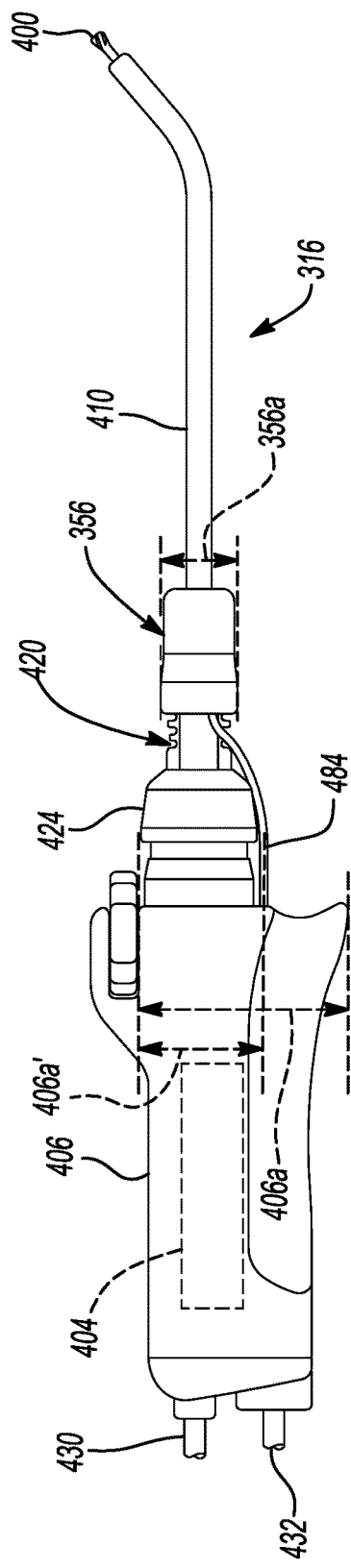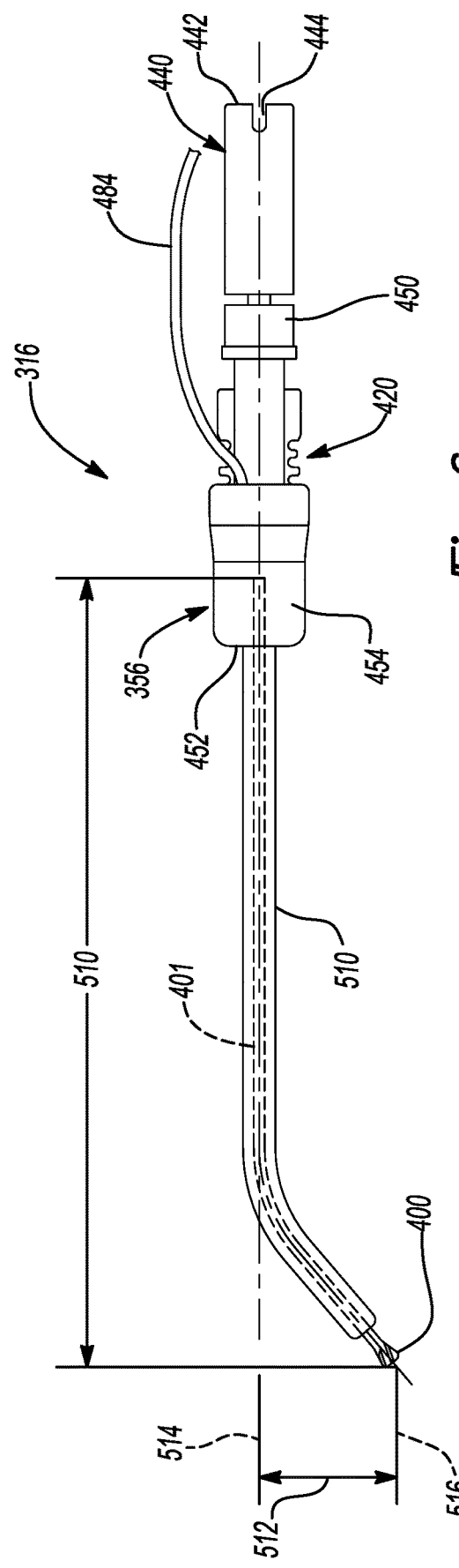
Fig-5
Fig-6

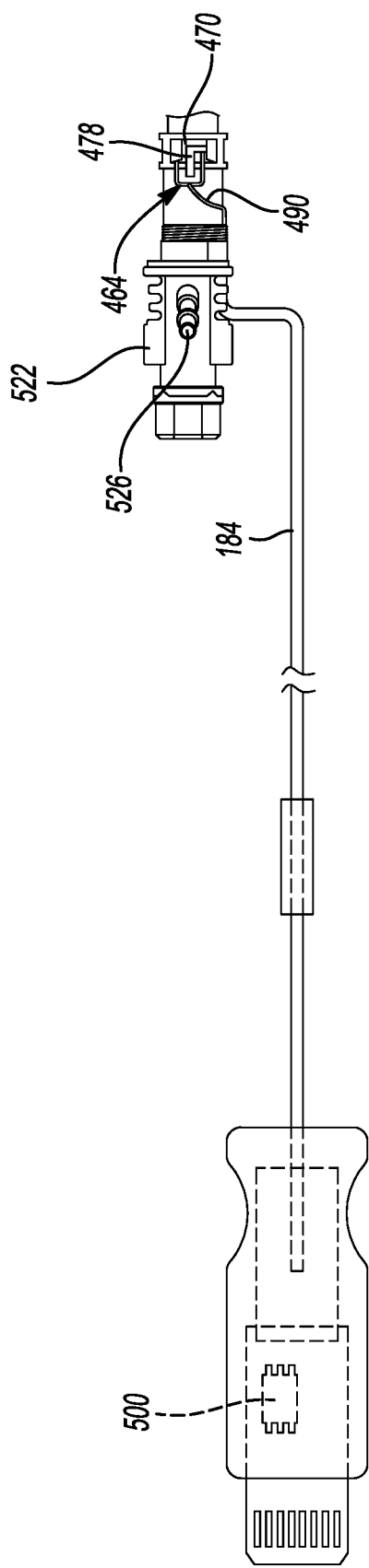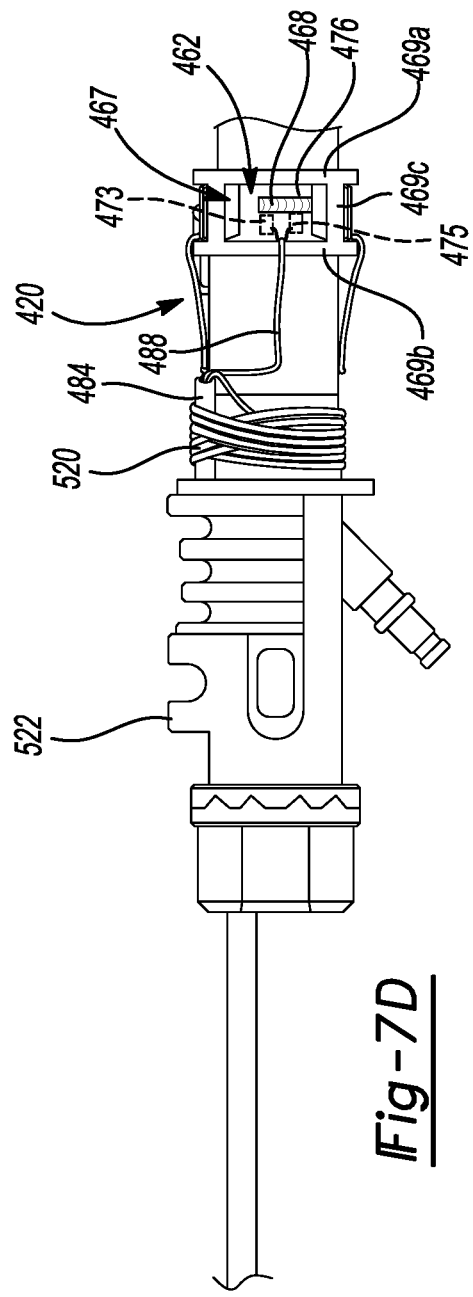

SYSTEM AND METHOD FOR CONNECTING AN INSTRUMENT

CROSS-REFERENCE TO RELATED APPLICATIONS

This application includes subject matter related to that disclosed in U.S. patent application Ser. No. 16/055,712, filed Aug. 6, 2018 and U.S. patent application Ser. No. 16/055,747, filed Aug. 6, 2018. The entire disclosures of the above applications are incorporated herein by reference.

FIELD

Disclosed is a system and method of operating and connecting an instrument, for example a rotatable instrument, and a motor or control.

BACKGROUND

This section provides background information related to the present disclosure which is not necessarily prior art.

A surgical instrument may be used during a procedure such as within a selected region of a subject's anatomy. The surgical instrument may be connected to a handle, the handle may include a motor or similar power system. The power system may rotate or otherwise move the instrument. The instrument, therefore, may provide selected operation relative to the handle. Further, multiple instruments may be connected to the handle. It may be selected, therefore, to operate different instruments in different selected manners and identification of the instrument may be useful.

SUMMARY

This section provides a general summary of the disclosure, and is not a comprehensive disclosure of its full scope or all of its features.

A driver may power an instrument, such as a burr or other resection or driven instrument during a selected procedure. The instrument may be removably connected to a driver, such as a powered tool handle. The powered tool handle may include a motor and a portion that is graspable by a user, such as surgeon.

The tool or tool assembly may include the handle that includes the motor and an instrument that is removably attachable to the handle and/or motor. Further, the tool assembly may be connected to a console or controller. The controller may include various additional features, such as power for the motor and an irrigation source. It is understood, however, that irrigation and power for the motor need not come from a single source.

The tool assembly may further include a connector that includes selected communication, power, and irrigation connection portions. The connector may include a transmitter to transmit a field that may couple with a receiving antenna to provide inductive power to selected components. Further, the connector may include an irrigation connection that may be connected to the handle and allow for maintaining the connection during removal and reconnection of one or more instruments with the handle.

In using the instrument during the procedure, the user may desire or select to navigate the instrument. In navigating the instrument, a tracked location of at least a portion of the instrument is determined. In tracking the instrument, a navigation system may determine and illustrate a position of the instrument relative to an image of the subject or patient for a selected period of time.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a perspective view of a tool and instrument, according to various embodiments;

FIG. 3 is a detailed cross-sectional view from FIG. 2;

FIG. 5 is a perspective view of a tool and instrument, according to various embodiments;

FIG. 6 is a detailed view of an instrument with a tracking device, according to various embodiments;

FIGS. 7A-7C are different plan views of an instrument hub and connector rotated around a long axis of the hub, according to various embodiments;

FIG. 7D is a detail view of a hub;

Corresponding reference numerals indicate corresponding parts throughout the several views of the drawings.

DETAILED DESCRIPTION

Figure 2:
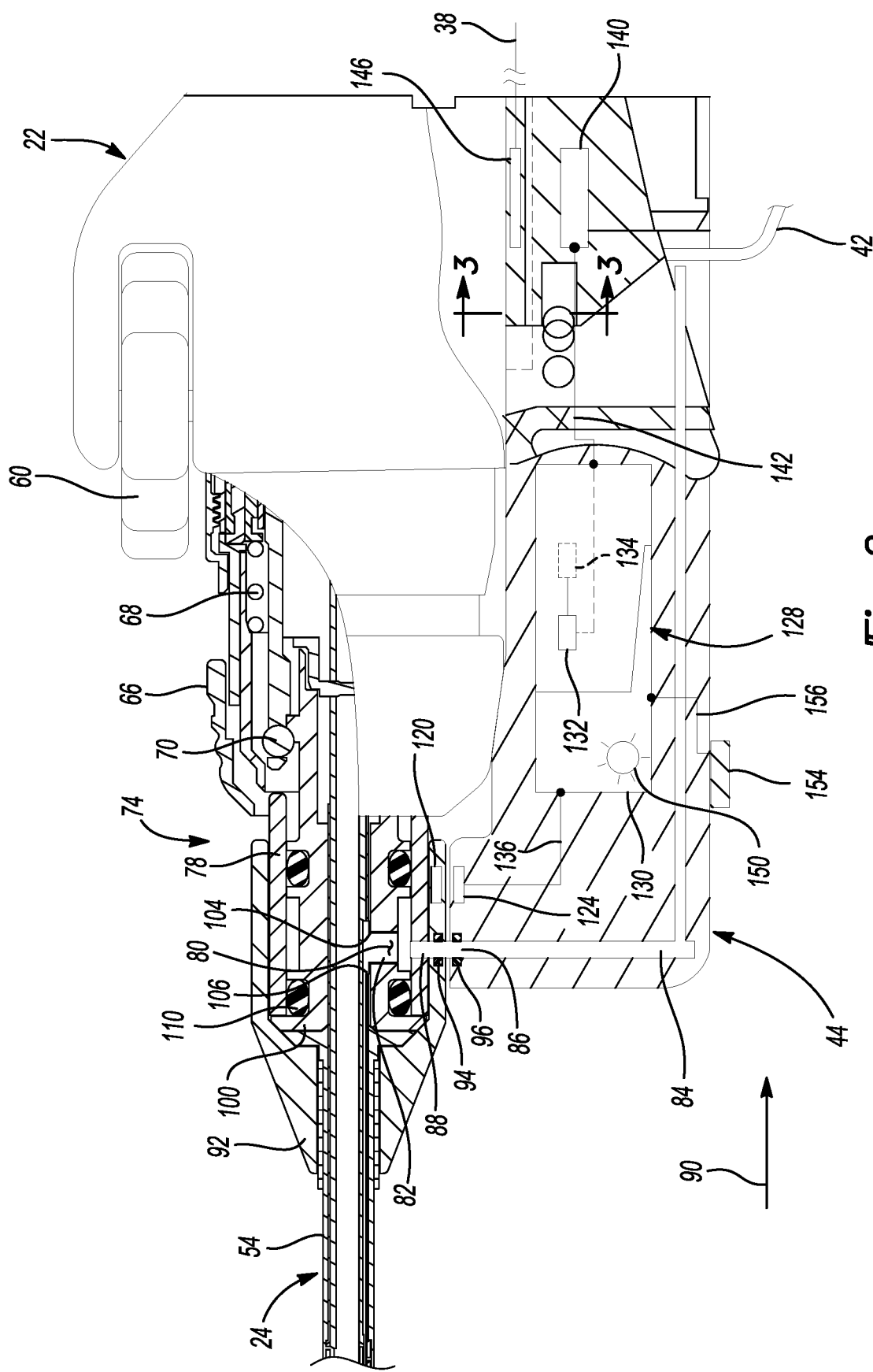
FIG. 2 is a cross-sectional view of the instrument assembly of FIG. 1.

Example embodiments will now be described more fully with reference to the accompanying drawings.

A tool assembly 20 is illustrated in FIG. 1. The tool assembly 20 includes a handpiece (hand-piece), handle portion, driver, or component 22 and an instrument portion 24. The handle portion 22 may include a housing 26 that houses various additional components, including a motor 28. The motor 28 may be powered in any appropriate manner, including electric, hydraulic, pneumatic, etc.

The tool assembly 20 is connected with an external system, which may include a control system which also may be referred to as a console or control system 34. The console 34 may have various connections with the tool assembly 20, such as including a suction or vacuum tube 36 from a vacuum source that connects to the handle 26, an electrical connection 38 that connects to the handle 26, and an irrigation line or connection tube 42. The console 34 may further include various portions or systems such as a tracking device and/or coil array controller, as discussed herein. The console 34 may, therefore communicate with or have communication connections with a navigation system 250 (FIG. 4) as discussed herein.

The irrigation tube 42 may connect with the handle housing 26, according to various embodiments, with a selected connection member or cartridge 44. The cartridge 44 may be removably connected with the handle housing 26, as discussed further herein. In various embodiments, the cartridge 44 may also include various additional connection or control portions and/or systems to assist in controlling the tool assembly 20 directly and/or through the console 34. The cartridge 44 may also be provided to allow for various connections, such as communication or power connections, with the console to provide communication and/or power to other portions connected to the handle 20.

Various other controls may also be provided to control the instrument assembly 20, such as with a switch 46 including a foot switch. The switch 46 may be used to selectively control the tool assembly 20 such as including speed of the motor 28, direction of rotation of the motor 28, and various other controls. It is understood that the instrument 24 may be controlled by the motor 28 such as selecting, altering, etc. speed and direction through control of the motor 28 and this may control the instrument 24.

Generally the instrument 24 may be an assembly and includes various portions such as a working end or a tip 50. The working end 50 may include a distal end of the instrument 24 that may interact with a selected subject, such as an animate subject, inanimate subject, or the like. In various embodiments, the working end of 50 may include a burr or resection instrument to remove a portion of a patient's anatomy during a procedure. The working end 50 can perform an operation or work at a selected worksite, such as in or on a subject, as discussed herein.

Accordingly, the working end 50 may be operated by the motor 28 for speed, direction, and the like. Further the instrument 24 may include an outer tube member 54 that may extend a distance along the instrument portion 24 toward the working end 50, however the working end 50 may be exposed. The tube 54 may define an internal cannula through which a shaft 56 extends. The shaft 56 may connect with the motor 28 to provide power to the working end or force to the working end 50 to move the working end 50. Accordingly, the shaft 56 and working end 50 may form a working instrument, such as a burr or other appropriate instrument.

The handpiece 22 can include various portions, similar to those generally included on other appropriate instruments, such as the Straightshot® M4 and/or M5 handpiece (i.e. debrider), sold by Medtronic, Inc. having a place of business in Minneapolis, Minn. For example, a turn dial or member 60 may be used to rotate a direction of the working end 50 relative to a central axis 62 of the handpiece 22 and/or the shaft 56. The handpiece 22 also includes a connection 66 that may include a chuck or quick connect assembly to allow connection of the instrument 24 to the handpiece 24 and/or the motor 28.

A quick connect assembly can include various features or elements, such as a biasing spring 68 and a catch or latching member or ball 70. The connection assembly 66 engages a hub assembly 74. The hub assembly 74 may include various portions, but generally includes a connection with the tube member 54 of the instrument 24. In particular, the hub assembly 74 may be integral with or formed with the tube 54 as a part of the instrument 24. In various embodiments, the hub assembly 74 engages the handle 22 via the hub assembly 74. Upon engagement of the hub assembly 74 with the handle assembly 22 via the connection assembly 66, the instrument 24 may then be operated by the handle 22, including the motor 28.

In various embodiments, the hub assembly 74 may include an internal hub member 76. The internal hub member 76 may be engaged by the locking or connection member 70 to hold the instrument 24 relative to the handle assembly 22. The operation of the quick connect assembly 66 may be similar to that of the Straightshot® M5 handle assembly, as discussed above.

The internal hub 24 may be surrounded by an irrigation hub or capsule 78. The irrigation hub 78 may surround the inner hub 76 and provide or form a holding volume or region 80 to hold an irrigation volume or fluid as it or prior to its passing through an irrigation passage 82 into the inner hub 76. Upon delivery or passage into the inner hub 76, an irrigation volume of fluid may pass down or through the shaft 56 to irrigate near the working end 50. The suction hose or source 36 may be used to draw a suction through the handle assembly 22 and through the instrument 24, such as through an innermost cannula. Accordingly, a constant irrigation and suction may be provided at the working end 50 of the instrument 24.

To deliver irrigation to the inner hub 76, such as through the irrigation hub 78, the cartridge 44 may include a passage, such as an irrigation passage 84. The irrigation passage 84 may extend through the cartridge 44 from the irrigation tube 42. The cartridge 44 and the irrigation tube 42 may be formed or provided as a single piece. For example, the irrigation tube 42 may be permanently connected to the cartridge 44. The cartridge 44 may be removably connected to the handle assembly prior to or during preparation of the handle assembly 22 for a procedure.

According to various embodiments, for example as illustrated in FIG. 3, the cartridge 44 may be connected to the handle assembly 22 with any appropriate connection. For example the handle assembly 22 may define or form a rail 88. The cartridge 44 may include an elongated groove or trough 90 that is complementary to the rail 88. The cartridge 44 may, therefore, be slid along the rail 88 by receiving or engaging the rail 88 within the groove 90. The cartridge 44 may then engage or include a locking feature that locks the cartridge 44 to the handle assembly. It is understood that any other appropriate connection, such as a snap fit, slide lock, screw connector, adhesive, or the like may be used to connect the cartridge 44 with the handle assembly 22. Regardless of the connection, however, the cartridge 44 including the irrigation passage 44 there through may connect the irrigation tube 42 with the inner hub assembly 76, as discussed further herein. Further, generally the cartridge 44 may be removed from the handle 22 at a selected time.

The cartridge 44, as illustrated in FIG. 2, includes the irrigation passage 84. In various embodiments, the cartridge 44 may be formed as a solid member and the passage 84 is formed as a bore through the cartridge 44. In various embodiments, however, the irrigation passage 84 and the cartridge 44 may include a tubing or tube member that extends from the irrigation tubing 42 through the cartridge 44 as the irrigation passage 84. Therefore, the cartridge 44 may be formed as a hollow member or shell portion that is connected to an end of the irrigation tube 42. A portion of the tube 42 extending through the cartridge 44 may form or define the irrigation passage 84 within the cartridge 44. Regardless, the cartridge 44 may be connected to the irrigation tubing 42 as a single piece. The cartridge 44 and the tubing 42, therefore, may be disposable and/or a single use. The cartridge 44 and the tubing 42 may be connected to an irrigation source, such as the console 34, and connected to the handle assembly 22. It is understood, however, that the irrigation source may be separate from the console, although controlled or flowing through the console 34. This may allow the cartridge 44 to be provided for a selected single procedure and discarded thereafter.

Regardless, the cartridge 44 may allow for a connection or positioning of an irrigation outlet 86 near or adjacent to an irrigation inlet 88 of the hub assembly 74. The inlet 88 may be formed as an opening or passage through a portion of the hub assembly 74, such as an external or outer hub member 92. The outer hub member 92 forming the inlet 88 may also include a seal portion or assembly, such as an O-ring 94. A complementary sealing assembly or portion, such as a second O-ring 96, may also be provided on or with the cartridge 44.

The cartridge 44 in being assembled to the handle assembly 22 may be moved in a direction of an arrow 98. Accordingly, the outlet 86 and the associated O-ring 96 may be moved toward or near the inlet 88 and the associated O-ring 94. Once the cartridge 44 is fully seated on the handle assembly 22, the O-rings 94, 96 may substantially make and form a fluid tight seal between the cartridge 44 and the handle assembly 22 for communication of an irrigation fluid. Irrigation fluid may flow from the irrigation supply, such as the console 34, to the hub assembly 74 of the instrument 24. In this way, the irrigation may be provided through the irrigation tube 42 and through the instrument 24 by connecting the cartridge 44 to the handle assembly 22 and forming a seal between the outlet 86 from the cartridge 44 and the inlet 88 at the hub assembly 74.

Accordingly, the cartridge 44 may be used to connect the irrigation source, such as from the console 34, with the instrument 24. The irrigation material, for example sterile water, may be passed through the instrument 24 such as around or through a cannula formed by the tube member 54. As illustrated in FIG. 2, the irrigation passage 84 may be provided to the hub assembly 74 through the inlet 82 of the outer hub 92 into the reservoir 80. The hub assembly 74 including the irrigating collar or hub portion 78 may surround a rotating or bearing hub portion 100. The rotating hub portion 100 may be engaged by the motor 28, such as with a driving shaft, to rotate the hub 94. It is understood, however, that the shaft 54 of the instrument assembly 24 may be connected directly to the motor 28, such as via drive shaft, and that the rotating hub 100 need not rotate. Rather, the instrument shaft 56 may rotate within the tubing member 54 to drive or rotate the working end 50.

The hub 100 may provide an internal passage 104 for the delivery of the irrigation material (e.g. fluid) from the irrigation passage 84 of the cartridge 44 to the area or region near the working end 50. The internal passage 104 through the inner collar 100 may allow for access through an opening 106 of the tubular member 54. Therefore, a fluid may pass through the irrigation passage 42 through the irrigation passage 84 in the cartridge 44 through the inlet 88 of the outer hub 92 and through the irrigation collar or hub member 78 to the inner collar or hub member 100. Selected sealing portions, such as one or more O-rings 94, 96 are provided to assist in sealing containing the irrigation fluid to pass through the selected passages and into the tube member 54. Irrigation may be provided from a selected source, such as the console 34, at a selected time through the cartridge 44 to the working end 50 of the instrument 24.

The cartridge member 44 may further include additional components and features, as discussed further herein. As discussed above, the cartridge 44 may provide for a connection of the irrigation supply to the instrument 24 through the irrigation passage 84 in the cartridge 44. Moreover, the cartridge 44, once assembled to the handle assembly 22, may be maintained in place even though instrument 24 may include a plurality of instruments that are intermittently and sequentially changed or switched.

For example, the instrument 24, illustrated in FIG. 2, may be removed from the handle assembly 22 and replaced with an alternative instrument. The assembly portion 66 may be used to disconnect the instrument 24 and replace it with an alternative instrument. The alternative instrument may be identical to the instrument 24, but replacing the instrument 24 such as after a certain work cycle. For example, the burr at the working end 50 may be operational or have peak efficiency for a selected period of time, such as five minutes, ten minutes, or the like. Therefore, the instrument 24 may be replaced with an identical instrument to maintain efficiency of the operation of the instrument 24. Alternatively, or in addition thereto, the instrument 24 may be replaced with a second or different instrument, such as a cutting or boring instrument. Regardless the instrument 24 may be disconnected from the handle assembly 22 and replaced with an alternative instrument.

The alternative instrument may include, however, a hub assembly substantially identical to or identical to the hub assembly 74 that is illustrated in FIGS. 1 and 2. Therefore, the hub assembly 74 of more than one instrument is connected with the handle assembly 22 by moving the instrument 24 generally in the direction of arrow 98. The hub assembly 74 of any instrument 24 may be positioned near the cartridge 44, as illustrated in FIG. 2. This allows for a connection of the irrigation from the irrigation source, such as the console 34, through the irrigation passage 84 and to the hub assembly 74 of any hub assembly connected to the instrument handle 22. The sealing assembly or connection, such as including the O-rings 94, 96, may still allow for a sealing connection of the irrigation passage to the instrument 24. The cartridge 44 need not be removed and/or is not removed from the handle assembly 22 even though the instrument 24 is removed and changed. The sealing assembly may allow for the irrigation to be provided through the irrigation passage 84 of the cartridge 44 without manipulating a connection with the hub assembly 74 separate from placing the instrument 24, including the hub assembly 74, onto the instrument handle assembly 22.

Further the instrument 24, such as at or near the hub assembly 74, may include an identification assembly or portion 120. In various embodiments, the identification member 120 may include a radio frequency identification tag or member. The ID member 120 may include a transmitting and/or receiving antenna assembly associated with a memory system. It is understood, however, that the ID 120 may also include a resonating antenna without a separate memory or communication transceiver assembly. The ID member 120 may be any appropriate ID member including those disclosed in U.S. Pat. App. Pub. No. 2016/0310218; U.S. Pat. No. 9,867,674; all incorporated herein by reference.

The cartridge 44 may include a receiving and/or transmitting antenna 124. The antenna 124, for example a transceiver, of the cartridge 44 may be connected to a selected electronics assembly and/or processor assembly 128. The electronics assembly 128 may include various elements or portions or components such as a printed circuit board 130 (PCB) on which various components may be mounted, such as a processor 132 and/or a memory 134. The processor 132 may be any appropriate processor such as a general purpose processor that is able to execute instructions stored on the memory 134 and access the instructions on the memory 134. The processor 132 may also include other appropriate or only include other appropriate processor systems, such as an application specific integrated circuit, a processor including internal memory or read only memory, or other appropriate processor systems. Nevertheless, the processor 132 may be provided on the circuit board 130 to communicate and/or control various components as discussed herein.

For example, the transceiver 124 may be energized to energize the ID 120 and/or receive a signal from the ID 120 and transmit a signal along or with a communication line 136 to the PCB 130. The signal from the transceiver 124 may be analyzed with the processor 132 to determine an identity of the instrument 24. The identity of the instrument 24 may be determined with the processor 132 at the electronics component 128 in the cartridge 44 and/or a signal may be transmitted from the PCB 130, including the processor 132, or directly from the transceiver antenna 124 to a cartridge antenna assembly 140. The cartridge antenna assembly 140 may include various features such as a radio frequency identification tag including selected power harvesting features or components such as NTAG I2C Explorer Kit, sold by NXP Semiconductors Austria GmbH, having a place of business in Gratkom. Communication between the cartridge antenna assembly 140 and the electronics component package 128 may be via a communication line 142, such as a wired connection. It is understood however, that the PCB 130 may be formed of a selected size and/or have a position such that the antenna assembly 140 is mounted or fixed to the PCB 130 and communication with the processor 132 may be via a trace formed on the PCB 130.

Regardless, the antenna 140 may receive a signal, such as a wireless signal, from a handpiece antenna 146. The handpiece antenna 146 may transmit a signal that communicates with the cartridge antenna assembly 140. The cartridge antenna assembly 140 may convert at least a portion of the signal into electrical energy (e.g. having a current induced) to power or assist in powering the electronics component 128.

The handpiece antenna 146 may also receive a signal from the antenna assembly 140 of the cartridge 44, such as the signal from the instrument ID 120 or other signals, as discussed further herein. The handpiece antenna 146 may be powered through the electrical connection 38 with the handpiece assembly 22, such as from the console 34. In various embodiments the electronics connection 38 may provide a signal, such as a power signal, to the handpiece antenna 146 substantially constantly, at a selected periodic rate, or based upon an input from a user.

The cartridge assembly 44, once connected to the handle assembly 22, can assist in provided identifying information of the instrument 24 to the console 34. In various embodiments, the identifying information may be used for determining operational parameters of the instrument 24, which may control the handle operation, such as motor speed, run time, and the like. The identification of the instrument 24 may be used to assist in navigating or tracking the instrument 24, such as a position of the working end 50 if navigation is to be determined for a selected period or procedure. For example, the geometry of the instrument 24 may be predetermined and saved with the ID 120 and/or recalled from a database based upon identification of the instrument 24. Accordingly, the identification of the instrument 24 may be transmitted to the console 34, or other appropriate portions, such as a navigation processor assembly as discussed below.

The ID member 120 may be used to allow for automatic identification of the instrument 24. The processor 132 may analyze the signal from the ID member 120 to identify the instrument 24 and/or the console 34, or other appropriate system. Regardless, the signal from the ID member 120 may be used by a selected processor system to identify the instrument 24 without further input from a user. The antenna 124 may be intermittently energized, such as once ever second, to interrogate any member, such as the ID member 120, that is present. The signal from the ID member 120 may then be received by the antenna 124 and transmitted, as discussed above. The antenna 124 may be energized at a selected interval, such as based on a predetermined rate where the antenna 146 from the handpiece 22 is used to energize the electronics component 128.

Also the identification, such as automatic identification, of the instrument 24 with the ID member 120 may be used to assist in identifying proper instruments for a selected procedure, such as identifying instruments for a selected portion of a procedure and/or usage during a procedure. In selected applications, the ID member 120 may have a specific identification or information regarding the specific instrument that is recalled from a database to assist in determining a work cycle or life of the instrument 24, such as number of sterilization cycles, or the like. In addition, the ID member 120 may have written thereto information regarding work cycles, and therefore the electronics assembly 128 may transmit a usage count when connected to the instrument handle 22.

The electronics assembly 128 of the cartridge 44 may further include various operational and/or communication features. For example, a display may be provided on the cartridge 44 that is powered through the antenna assembly 140 harvesting electrical power from the signal from the handpiece antenna 146. In various embodiments, a low power or low current emitter, such as a light emitting diode 150 may be provided on the cartridge 44. The LED 150 may be viewed by the user 200 (FIG. 4) to assist in identifying a condition, operational control, or the like of the instrument assembly 20. The LED 150 may have a selected blink rate, color, or other feature to provide identification to the user 200 of operational conditions of the instrument assembly 20. For example, the LED 150 may glow or emit a solid green light to indicate that the handpiece 22 is connected properly to the console 34 and/or that the instrument 24 is connected properly to the instrument handle assembly 22. The LED 150 may then change color and/or blink rate to indicate power and/or rotational direction of the working end 50. For example, a solid yellow may indicate a clock wise rotation while a blinking yellow may indicate a counter clockwise rotation. Other colors or blink rates may be used to identify different operational conditions of the instrument assembly 20. The LED 150 may also be used to indicate a state of the control system such as irrigation supply volume being empty or near empty, vacuum or suction is proper, etc.

The processor 132 may control the LED 150 directly and/or transmit signals to the LED 150 from the console 34. For example, the LED 150 may receive a signal from the console 34 regarding the rotation of the instrument assembly 20 to the console 34. Alternatively, or in addition thereto, a signal may be transmitted to the processor 132 regarding the connection of the instrument assembly 20 to the console 34 and the LED 150 may be controlled from the processor 132. Again the LED 150 may be connected to the cartridge 44, such as an external wall thereof, and/or mounted on the PCB 130.

The cartridge 44 may further include controls, such as one or more push buttons or switches 154. The controls 154 may be used for operational control of the instrument assembly 20. For example, as discussed above, the footswitch 46 may be used to control the instrument assembly 24 via the console 34. In addition and/or alternatively to the footswitch 46, the control 154 may be used to control the instrument assembly 20. In various embodiments, the footswitch 46 may be eliminated and the control 154 of the cartridge 44 may be used to operate the instrument assembly 20.

The control 154 may be dedicated to a selected control of the instrument assembly and/or changed based upon a signal received with the control 154 and/or the console 34. For example, the control 154 may be used to change the rotational direction of the working end 54. As discussed above the LED 150 may be used to indicate the directional control of the working end 50 based upon input from the control 154. Further, the control 154 may be used to alternatively and/or additionally, control irrigation supply through the irrigation passage 84, suction through the suction assembly 36, or other appropriate features or controls of the tool assembly 20. In various embodiments, the control 154 may include one or more control portions of elements (e.g. such as one or more push buttons) and may control one or more features of the tool assembly such as such as to change irrigation flow or rate, change speed of the instrument, flush the instrument, and/or perform other functions.

The control 154 may be connected to the PCB 130 directly, such as mounter thereon, and/or via a connection, such as a wire connection 156. The control 154 may provide a signal to the console 34 directly, the processor 132 directly, or indirectly to one or both. Accordingly, the control 154 may be used to control various features of the instrument assembly 20. Again the signal from the control 154 may be transmitted to the console 34 through the antenna assembly 140 and the cartridge 44 to the antenna assembly 146 of the handpiece 22. The signal from the controller 154 may be transmitted through the electronics assembly 128, including initially processed thereon and then transmitted to the console 34. The control 154 may be used to control the handpiece assembly 22 via the console 34. In additional, or alternatively thereto, the control 154 may control the handpiece assembly directly such as through the electronics component 128 having sent a signal transmitted from the cartridge assembly 140 to the handpiece antenna 146. The control 154 may be used to communicate with the console 34, such as for operation of the instrument assembly 20, and/or directly controlling the handpiece assembly 22 (e.g. the motor operation, including speed).

It is understood that the electronics component 128 may include further or additional controls in addition to those discussed above. Moreover, the cartridge 44 may include connections to various other components of the handpiece assembly 22 and/or the instrument 24. Regardless, the cartridge 44 may be efficiently connected to the handpiece assembly 22 and maintained during a selected procedure although the instruments assembly 24 is removably replaced with the handpiece assembly 22. The cartridge assembly 24 may further be connected to the handpiece assembly 22, such as to the handle 26, while maintaining or including a selected dimension 164. The dimension 164 may allow for operation of the instrument assembly 20, even with the connected cartridge 44 to the handle assembly 22, by single hand 202 of a human user. The instrument assembly 20, including the cartridge 44, may therefore be used by the user 200 for a selected procedure by the single hand 202 so that a second hand 204 of a user may be free for other tasks.

Further, as discussed above, the handle assembly 22 may be maintained for multiple procedures while the cartridge 44 may be provided as a single use. The cartridge 44 may therefore be delivered to a procedure in a substantially sterile manner and/or packaging to allow for ease of connection of various portions, such as the irrigation tubing 42, to the handle assembly 22 and the instrument assembly 24.

Further, the cartridge 44 may allow for connection of all connections from the console 34 to the handle assembly 22, such as the electronics connection and/or suction connection. It is understood, however, that the cartridge 44 may be substantially efficiently manufactured and manufactured at a low price manner by having power provided thereto from the handpiece antenna 146 rather than including internal batteries or other power components.

Figure 4:
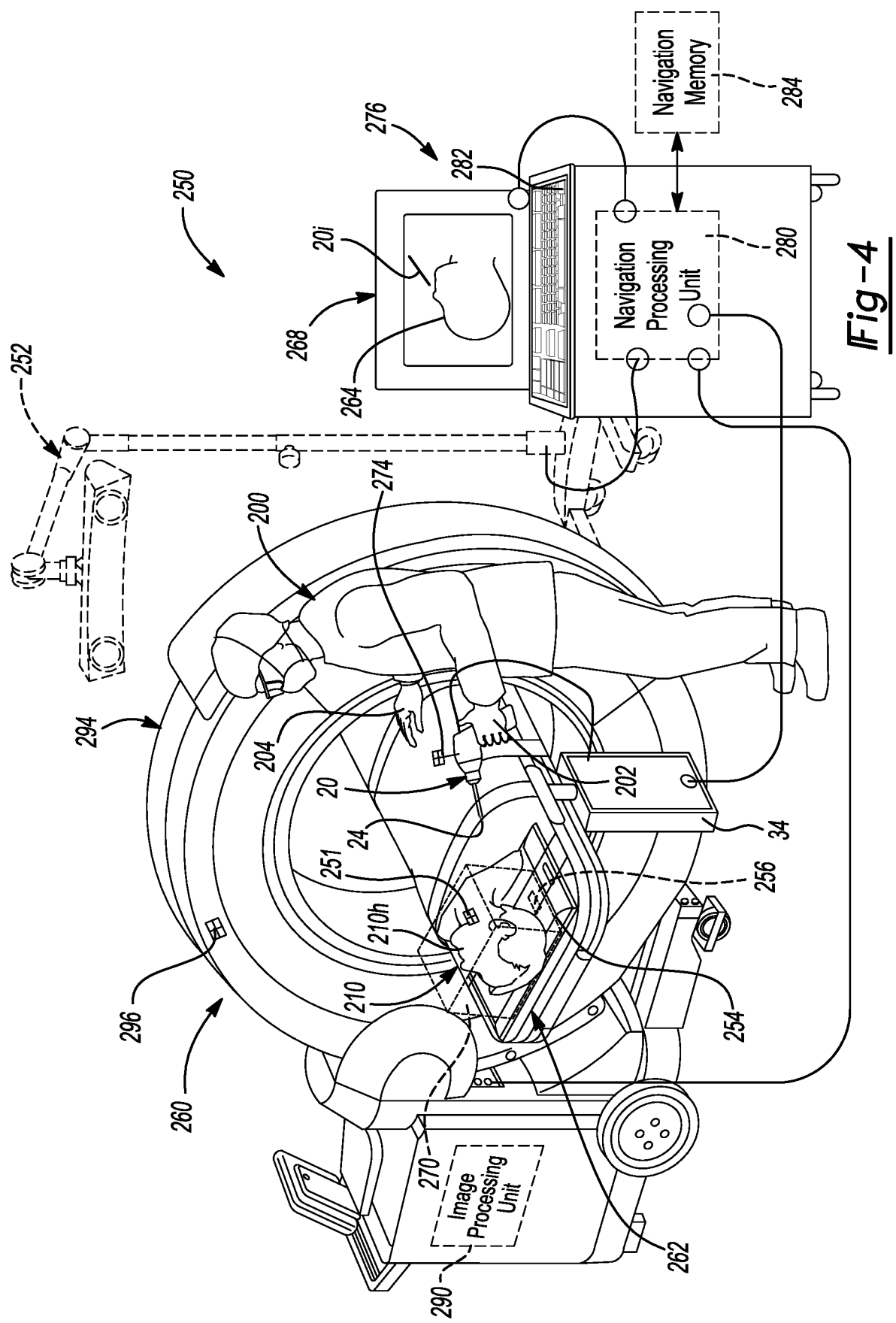
FIG. 4 is an environmental view of the instrument assembly.
Figure 7A:
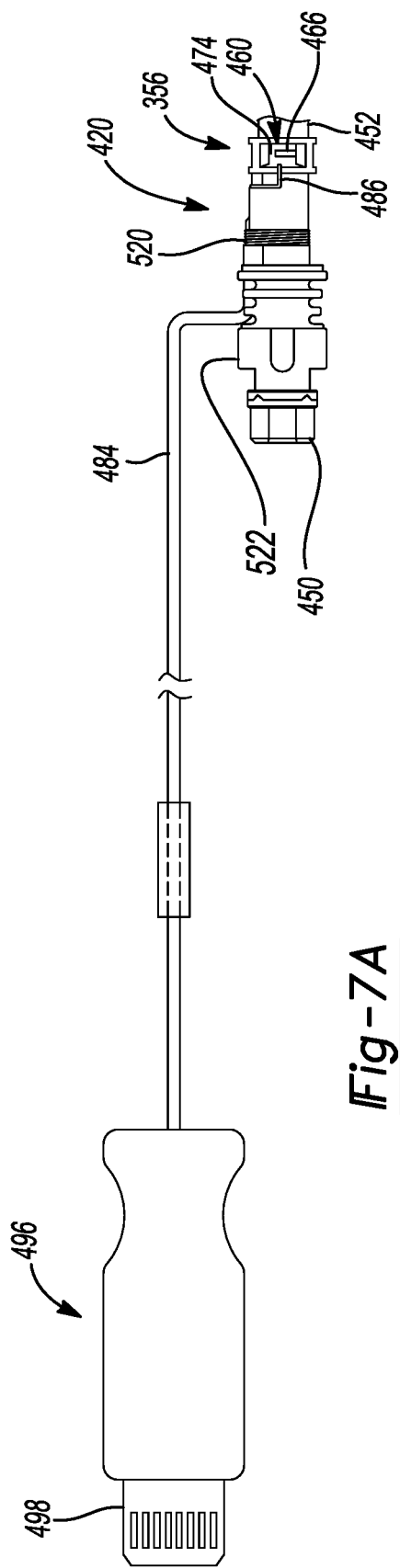
Figure 7B:
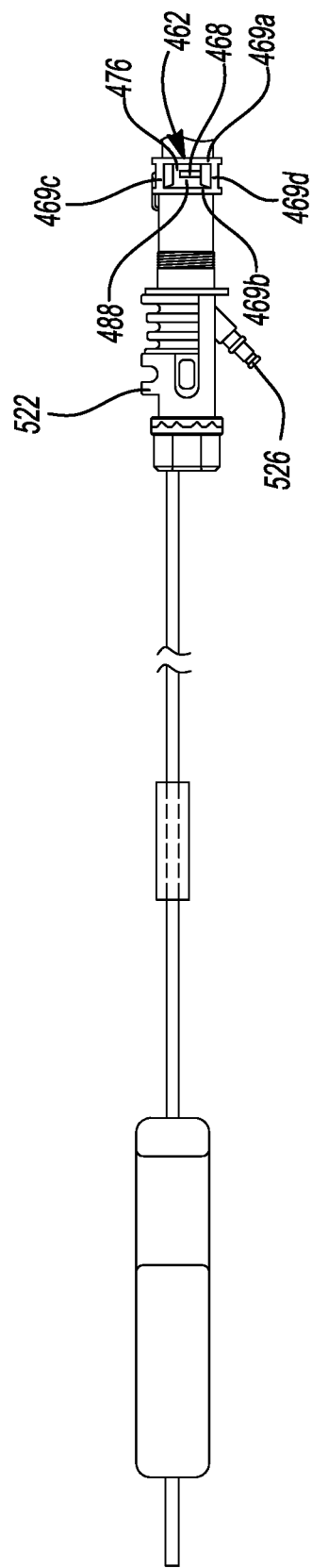

As illustrated in FIG. 4, the instrument or tool assembly 20 may be used by the user, such as a human user 200. The user 200 may hold the handpiece 22 in the single hand 202 to manipulate and operate the tool assembly 20. As discussed above, the hand 202 of the user 200 may contact the control 154 for controlling the tool assembly 20, such as for speed, direction, start/stop, etc. The user 200 may also view the indicator, such as the LED 150. The user 200 may also connected the cartridge 44, the instrument assembly 24, and/or other portions to the handpiece 22. It is understood, however, that a different user, such as a scrub nurse, may connect the cartridge 44 and/or the instrument 44 to the handpiece 22.

The user 200 may use the tool assembly 20 for various procedures. In various embodiments, the instrument assembly 24 may be useful in a selected ear, nose, or throat procedure. For example, the instrument assembly 24, including the working end 50, may be useful to remove tissue in a sinus passage in a subject 210. The subject may be a human patient. It is understood, however, that the subject need not be a human person, or any living object. The subject may be any workpiece, such as an airframe, computer assembly, etc.

Regardless, with reference to FIG. 4, the instrument assembly 20 may be used to perform a procedure on the subject 210. Selected procedures may include viewing images of the subject 210, acquiring images of the subject 210, and/or navigating the instrument 24, such as the working end 50, relative to the subject 210. As illustrated in FIG. 3, the procedure may be performed by the user 200 relative to the subject 210.

With reference to FIG. 4, in various embodiments, the procedure using the instrument assembly 20 may be a navigated procedure that uses a navigation system 250. It is understood that navigation is not necessary for use with the instrument assembly 20, but it may be selected. In various embodiments, for example, the user 200 may directly view within a nostril of the subject 210 for performing the procedure. Also, non-human subjects may have the procedure and navigation may not be selected or necessary. Further, images acquired with an imaging system to image through the subject 210 may not be selected or necessary. Imaging system may include an endoscope or direct viewing devices.

If selected, the procedure may include the navigation system 250 which may include various components that assist in navigating the procedure including a selected tracking system. The tracking system may include various components or portions such as various localizers. Various localizers may include an optical tracking system that may include an optical localizer 252 and/or an electromagnetic tracking system that includes a Tracking Coil Array (TCA) 254. While an optical tracking system may be used with the TCA 254, it is understood that only one tracking system, such as including the TCA 254, may be used with the navigation system 250. Also, both an optical localizer 252 and the TCA 254 may be used together or simultaneously for tracking one or more instrument. The instrument assembly 20, or portion thereof, may be tracked during a selected procedure, such as a navigated procedure with the navigation system 250.

The TCA 254 may include one or more conductive coils 256 positioned relative to a subject 210 on which a procedure is performed. In various embodiments, a procedure may be performed on or near a head 210h of the subject 210. As discussed in further detail herein, a subject tracking device or assembly 258 may be connected to the subject 210, such as to the head 210h of the subject 210. The tracking assembly 258 may also be referred to as a Dynamic Reference Frame (DRF) or a patient tracker.

With continuing reference to FIG. 4, the navigation system 250 may include various features or elements as discussed below. Generally, the navigation system 250 may be used to determine or track a position of the instrument assembly 20 in a volume. The position may include both a three dimensional X,Y,Z location and orientation. Orientation may include one or more degrees of freedom, such as three degrees of freedom. Thus, a total of at least six degrees of freedom may be determined for the position of the instrument assembly 20.

Tracking the position of the instrument assembly 20 may assist the user 200 in determining a position of the instrument assembly 20, even if the instrument assembly 20 is not directly viewable by the user 200. Various procedures may block the view of the user 200, such as performing a repair or assembling an inanimate system, such as a robotic system, assembling portions of an airframe or an automobile, or the like. Various other procedures may include a surgical procedure, such as performing a spinal procedure, neurological procedure, positioning a deep brain simulation probe, or other surgical procedures on a living subject. In various embodiments, for example, the living subject may be a human subject 210 and the procedure may be performed on the human subject 210. It is understood, however, that the instrument assembly 20 may be tracked and/or navigated relative to any subject for any appropriate procedure. Tracking or navigating an instrument for a procedure, such as a surgical procedure, on a human or living subject is merely exemplary.

Nevertheless, in various embodiments, the surgical navigation system 250, as discussed further herein, may incorporate various portions or systems, such as those disclosed in U.S. Pat. Nos. RE44,385; 7,697,972; 8,644,907; and 8,842,893; and U.S. Pat. App. Pub. Nos. 2004/0199072, all incorporated herein by reference. Various components that may be used with or as a component of the surgical navigation system 250 may include an imaging system 260 that is operable to image the subject 210, such as an O-arm® imaging system, magnetic resonance imaging (MRI) system, computed tomography system, etc. A subject support 262 may be used to support or hold the subject 210 during imaging and/or during a procedure. The same or different supports may be used for different portions of a procedure.

Image data may be acquired during a surgical procedure or acquired prior to a surgical procedure for displaying an image 264 on a display device 268. The instrument assembly 20 may be tracked in a trackable volume or a navigational volume that is produced by a transmitter antenna or transmitting coil array that is incorporated into the localizer 254, as illustrated in FIG. 4. The position of the instrument assembly 20 may be tracked in the tracking volume relative to the subject 210 and then illustrated as an icon 20i with the display device 268. In various embodiments, the icon 20i may be superimposed on the image 264 and/or adjacent to the image 264. As discussed herein, the navigation system 250 may incorporate the display device 268 and operate to render and display the image 38, from image data. Also, the determined position of the instrument assembly 20 may be performed and displayed with the display device 268, such as the icon 20i.

With reference to FIG. 4, the electro-magnetic (EM) localizer that is operable to generate electro-magnetic fields with coils 256 of the transmitting coil array (TCA) 254 which is incorporated into the localizer 254. The TCA 254 may include one or more coil groupings or arrays. In various embodiments, more than one group is included and each of the groupings may include three coils, also referred to as trios or triplets. The coils may be powered to generate or form an electro-magnetic field by driving current through the coils of the coil groupings. As the current is driven through the coils, the electro-magnetic fields generated will extend away from the coils 256 and form a navigation domain or volume 270, such as encompassing all or a portion of a head 210h, spinal vertebrae, or other appropriate portion. The coils 256 may be powered through the console 34. It is understood, however, that the TCA 254 may be controlled with a controller separate from the console 34, when selected.

The navigation domain or volume 270 generally defines a navigation space or patient space. As is generally understood in the art, the instrument assembly 20, such as a drill, lead, etc., may be tracked in the navigation domain relative to a patient or subject with an instrument tracking device 274. For example, the instrument assembly 20 may be freely moveable, such as by the user 200, relative to the DRF 251 that is fixed relative to the subject 210. Both the tracking devices 251, 270 may include tracking or sensing coils (e.g. conductive material formed or placed in a coil) that senses and are used to measure a magnetic field strength, etc. Due to the tracking device 270 connected or associated with the instrument assembly 20, relative to the DRF 251, the navigation system 250 may be used to determine the position of the instrument assembly 20 relative to the DRF 251. The tracking device 270 may be selectively placed on the instrument assembly 20, such as connected to the handpiece 22 and/or nearer the instrument 24 similar to the Straightshot® M4 navigated ENT instruments, as sold by Medtronic, Inc. It is further understood that the tracking device may be any appropriate tracking device, such as an optical, acoustic, or the like tracking device.

The navigation volume or patient space may be registered to an image space of the patient and the icon 20i representing the instrument assembly 20 may be illustrated at a navigated (e.g. determined) and tracked position with the display device 268, such as superimposed on the image 264. Registration of the patient space to the image space and determining a position of a tracking device, such as with the tracking device 270, relative to a DRF, such as the DRF 251 may be performed as generally known in the art, including as disclosed in U.S. Pat. Nos. RE44,385; 7,697,972; 8,644,907; and 8,842,893; and U.S. Pat. App. Pub. Nos. 2004/0199072, all incorporated herein by reference.

The navigation system 250 may further include a navigation processor system 276. The navigation processor system 276 may include the display device 268, the localizer 254, the console 34, and other portions and/or connections thereto. For example, a wire connection may be provided between the console 34 (together or separate from a TCA controller) and a navigation processing unit 280. Further, the navigation processor system 276 may have one or more user control inputs, such as a keyboard 282, and/or have additional inputs such as from communication with one or more memory systems 284, either integrated or via a communication system. The navigation processor system 276, according to various embodiments, may include those disclosed in U.S. Pat. Nos. RE44,385; 7,697,972; 8,644,907; and 8,842,893; and U.S. Pat. App. Pub. Nos. 2004/0199072, all incorporated herein by reference, and/or may also include the commercially available StealthStation® or Fusion™ surgical navigation systems sold by Medtronic Navigation, Inc. having a place of business in Louisville, Colo.

Tracking information, including regarding the magnetic fields sensed with the tracking devices 251, 270, may be delivered via a communication system, such as the console 34, which also may be a tracking device controller, to the navigation processor system 276 including the navigation processor 280. Thus, the tracked position of the instrument assembly 20 may be illustrated as the icon 20i relative to the image 264. Various other memory and processing systems may also be provided with and/or in communication with the processor system 276, including the memory system 284 that is in communication with the navigation processor 280 and/or an imaging processing unit 290. The image processing unit 76 may be incorporated into the imaging system 260, such as the O-arm® imaging system, as discussed above. The imaging system 260 may, therefore, include various portions such as a source and a x-ray detector that are moveable within a gantry 294. The imaging system 260 may also be tracked with a tracking device 296. It is understood, however, that the imaging system 260 need not be present while tracking the tracking devices, including the instrument tracking device 270. Also, the imaging system 260 may be any appropriate imaging system including a MRI, CT, etc.

Information from all of the tracking devices may be communicated to the navigation processor 280 for determining a position of the tracked portions relative to each other and/or for localizing the instrument assembly 20 relative to the image 264. The imaging system 260 may be used to acquire image data to generate or produce the image 264 of the subject 210. It is understood, however, that other appropriate imaging systems may also be used. The console 34 may be used to operate and power the TCA 254, as discussed above.

Moreover, as discussed above, the icon 20i may be based on the signal received and processed form the ID 120. The ID 120 associated with the instrument 24 may be used to determine the position of a selected or predetermined portion of the instrument assembly 20. The determined positioned, in light of the identification of the instrument 24, may be incorporated into the icon 20i. Specific geometry and similar features may be displayed and used to determine a specific position of a portion of the instrument 24 that is spaced away from the tracking device 270.

Also, the information related to the ID 120 and the instrument 24 may be displayed on the display device 268. Information may include end of life cycle, sterilization indication, connection features, etc. Thus, the information collected from the ID 120 or recalled from a database may be displayed with the display device 268.

Regardless of the specific tracking system or technology, information from all of the tracking devices may be communicated to the navigation processor 290 for determining a position of the tracked portions relative to each other and/or for localizing the instrument 20 relative to the image 264. The imaging system 260 may be used to acquire image data to generate or produce the image 264 of the subject 210. It is understood, however, that other appropriate imaging systems may also be used. In various embodiments, the instrument 20 may include various features and/or portions as discussed above and herein. In various embodiments, with reference to FIG. 5, FIG. 6, FIG. 7A-7D, an instrument 316 may include various portions such as a distal or working end 400. The instrument 316 may also include various features or portions as the instrument 20, discussed above, in addition and/or alternatively to those discussed herein.

The working end 400 may be formed as a selected instrument working end or portion, such as a burr, grinder, cutter, or cutting tool that is rotated by a motor 404 within a handle or tool handle 406. The tool handle 406 may be held with a single hand of the user 200 and be operated by the user 200. In various embodiments, a foot switch is provided to power on and off the motor 404 while the user holds the handle 406. The instrument 316 may further include an elongated tube or shaft 410. The elongated tube 410 may include an internal and/or external portion, such as the tools sold with the StraightShot® M5 power handle, by Medtronic, Inc., having a place of business in Minneapolis, Minn. In various embodiments, the shaft 410, may be included as an elongated tube or a tubular shaft.

The instrument 316, including the elongated tube 410, may include an exterior wall having an interior cannula through which the working end 400 is powered, such as by an elongated shaft 401 to drive the working end 400. As discussed further herein, the shaft 401 driving the working end 400 may connect with the motor 404 through a hub 420. The hub 420 may engage a collet 424 to hold or fix the instrument 316 relative to the handle 406.

In various embodiments, irrigation may be provided through the instrument 316, such as through or by an irrigation barb 526. It is understood that the irrigation barb 526 may be connected with an irrigation hose or tubing to provide irrigation through the instrument 316. Further, suction may be drawn or pulled through the instrument 316, and through the handle 406, such as through a suction tube 430. The suction tube 430 and an electrical connection line 432 may be connected to a console or controller, which may be incorporated with the TCA controller 52. It is understood that the console or controller may be similar to the console Medtronic IPC® power and control console or System, sold by Medtronic, Inc. Nevertheless the instrument 316 may be moved and powered by the handle 406 when operated by the user 200.

In various embodiments, the tracking device 356 may be incorporated into or onto the hub 420. With exemplary reference to FIG. 3-4C, the tracking device 356 may be incorporated onto the hub 420 of the instrument 316. The hub 420 of the instrument 316, as illustrated in FIG. 3, may be connected to the shaft 410 through which the shaft 401 of the bit or working end 400 passes. The shaft 401 extends through the hub 420 and may terminate and/or engage a tongue 440. The tongue 440 may terminate and/or have a terminal end 442. The terminal end 442 may have a keyed or engaging portion, such as an engaging wall 444 to engage an internal element in the handle 406. For example, a shaft extending from the motor 404 may engage the engaging wall 444 of the tongue 440. An interference between the shaft extending from the motor 404 and the engaging wall 444 may allow for transfer of forces from the motor 404 to the tongue 440. As the tongue 440 is connected to the bit shaft 401, the working end 400 may then rotate due to a force transferred through the tongue 440. The shaft 401, passing through the hub 420, may allow for the hub 420 to be positioned or moveable relative to the handle 406 and carry various components, such as the tracking device 356 relative thereto.

Generally, the bit shaft 401, working end 400, tongue 440, and hub 420 components are provided as a single assembly, such as from a supplier. Thus, the user 200 may connected the instrument 316 to the handle 406, including the motor 404, as a single action or assembly. Further, the instrument may be a single use or one time use instrument. This allows the instrument to be useable with the handle 406 for the procedure, including tracking of the instrument 316, while allowing ease or assembly and efficient sterile preparation and disposal.

The hub 420 is illustrated in greater detail in FIGS. 4A, 4B, and 4C and discussed below. A detail view of the hub 420 is illustrated in FIG. 4D. Initially, the working end 400 and the associated shaft 401 may be formed of a selected material, such as a metal or metal alloy. In various embodiments, the shaft 410 of the instrument 316 may also be formed of a selected metal or metal alloy material. The hub 420 may be formed as a single member either with the shaft 410 or separate therefrom. For example, the hub 420 may be formed of a selected polymer material that may be over molded or injection molded onto the shaft 410. It is understood, however, that the hub 420 may be formed separately from the shaft 410 and connected during assembly of the instrument 316. Moreover, it is understood that the hub 420 may be formed of selected appropriate materials such as polymers, co-polymers, metal alloys, selected bearing materials, combinations thereof, or the like.

The hub 420 generally extends from a proximal end 450 to a distal end 452. The proximal end 450 and distal end 452 may further be terminal ends of the hub 420. As illustrated in FIG. 3, and discussed further herein, at least a portion of a distal portion, such as extending from the distal end 452 toward the proximal end 450, may be a covering or encapsulation 454. The encapsulation portion or member 454 may include a wrapping or shrink wrap formed over selected portions of the hub 420, as discussed further herein. It is further understood that the cover 454 may a rigid member that is passed on to the hub 420, such as over the shaft 410. The tracking device 356, even when covered, may have an external dimension (e.g. cross-sectional diameter) 356a that is less than or equal to an external dimension 406a of a portion of the handle near or adjacent to the hub 420 and/or external dimension 406a' of a chuck or instrument attachment. Thus, the hub 420 including the tracking device 356 may allow a large field of view and efficient operation of the instrument 316 and the handle 406.

For example, positioned on and/or fixed to the hub 420 may be a plurality of tracking elements or members that form the tracking device 356. The tracking elements may include a first tracking coil assembly 460, a second tracking coil assembly 462, and a third tracking member 464. Each of the tracking members 460, 462, 464 may incorporate or form a portion of the tracking device 356. For example, each of the member portions 460, 462, 464 may include a coil, such as a micro coil 466, 468, 470, respectively. The coils 466-470 may be formed around an inner core or a magnetically permeable core and positioned relative to a contact member or support. The coils 466-470 may be formed of a selected wire or connective material of a selected diameter. For example, the coils are formed by winding around an air core or selected core and in selected ends. Each of the coils 466-470 may be placed or connected to a board, such as a printed circuit board 474, 476, 478, respectively. The ends of the coils 466-470 may be mounted or fixed to selected conductive portions of the respective boards 474-478.

With reference to FIG. 4D, the coil assembly 462 is illustrated in greater detail. The hub 420 may include various mounting or fitting portions. For example, a well or holding region 467 may be defined by walls. An end wall 469a, a proximal wall 469b, and one or more side walls 469c, 469d may extend from a surface of the hub 420. The walls 469 may form or define the well to receive or hold the coil assembly 462 in a selected position, including location and orientation relative to the hub 420. The well may assist in manufacturing such as that the coil assembly 462 is positioned in a selected and appropriate position for each hub 420. Further, each of the coil assemblies may be placed in similar wells.

The coil 468 may include ends of the coiled wire that are mounted to the board 476, such as to pads. The board 476 may include traces to additional pads 473, 475. The pads 473, 475 on the board 476 allow for a connection, such as an efficient and repeatable connection, of the connector 488. Again, one skilled in the art will understand that each coil assembly may include a similar assembly.

The coil and board assemblies may then be fixed to the hub 420 in a selected manner. For example, the coils may be respectively epoxied or adhered to the respective boards 474-478. The epoxied assemblies may be adhered or epoxied to the hub 420, such as into the well or pockets 467. Generally, the member portions 460, 462, 464 generally have similar or identical dimensions and a generally rectangular shape having dimensions of about 2 millimeters (mm) to about 6 millimeters per side, where measurements may include a measurement and/or manufacturing tolerance of about 0.01 mm to about 2 mm. Exemplary dimensions may include about 5 mm by about 3 mm, about 3 mm by about 2 mm, about 3.05 mm by 3.81 mm, and about 2.54 mm by about 5.33 mm. Generally, the member portions may have an area of about 13 $mm^2$, including less than about 20 $mm^2$, less than about 15 $mm^2$ and about less than about 8 $mm^2$.

Further, a connector or communication line 484 may have selected twisted pair wires leads for each of the boards, such as a first lead 486, a second lead 499, and a third lead 490. Each of the respective leads 486-490 may also be fixed to the respective boards 474-478. It is understood that the respective leads 486-490 and the terminal ends of the coils 466-470 may be soldered or selectively affixed to the respective boards 474-478, as is generally understood in the art.

The leads may pass along the common connector line 484 to a proximal connector 496. The connector 496 may include a physical connection 498 to a selected console or assembly, such as the TCA controller 34. As discussed herein navigation or tracking information from the tracking device 356 may be transmitted along the common connector 484 to the connector 496 and the physical connection 498.

In the connector 496, in various embodiments, the physical connector 498 may include a selected memory and/or processor assembly 500. The memory and/or processor assembly 500 may include information regarding the instrument 316 to which the hub 420 is affixed. Information may include a geometry, such as a geometric position of the working end relative to the tracking device. For example, the information may include a distance 510, along an axis 514 of the instrument 316, from the tracking device may be the information. In addition and/or alternatively thereto, the information may include an offset distance 512 from the axis 514 of the instrument 316 to a working terminal end plane or position 516 of the working end 400.

Accordingly, the memory and/or processor assembly 500 may have calibrated a predetermined or known positions of the working end 400 relative to the tracking device 356 stored thereon. The stored information may be transferred to the navigation system 10 when the physical plug 498 has attached to the TCA controller 52. In transmitting the information, such as with a signal from the memory and/or processor assembly 500 to the navigation processor system 66, the processor system 66 is able to access or determine the calibrated position of the working end 400 relative to the tracking device 356.

The hub 420 may further include other components such as a fixation portion or member 520 to assist in holding the single line 484 relative to the hub 420. The fixation 520 may be a selected adhesive, wrapping, insulation wrapping, or the like. Further the hub 420 may include selected connection features, such as keyed or non-cylindrical features 522 which may include interference walls or facets. Further, the hub 420 may include an irrigation line connection, such as hose barb 526 to allow for a connection of an irrigation line to the hub 420. In various embodiments, the irrigation line may be connected to the barb 526 to provide a delivery of fluid through the hub 420 and thereafter through the shaft 410 around the working end 400. A suction may also be provided through a second inner cannula due to the suction line 430, as discussed above.

To assist in tracking the instrument 316, or portions thereof, the tracking device 356 includes the tracking members 460, 462, 464 that are selectively positioned on the hub 420. For example, each of the respective coils 466-470 may be positioned at about 400 to about 450 degrees, including about 420 or exactly 420 degrees, around the axis 514 relative to one another. It is understood that the tracking members 460-464 may be selectively positioned for various purposes.

Each of the respective coils 466-470 may be orthogonally positioned relative to one another. The field generated by the TCA 254 may then be sensed by the coils 466-470 positioned on the hub 420. That is the first coil 466 may sense a field that has a main axis that is substantially perpendicular to field sensed by the second coil 466 and the third coil 470. To sense the field in the selected orientations, the respective coils 466-470 may be positioned on the respective boards 474-478 in a selected manner or each of them may be formed connectively and positioned at different orientations on the hub 420. It is understood, by one skilled in the art, that the coils 466-470 may also generate respective fields (e.g. orthogonal to one another) that are sensed by the TCA 254 for tracking of the tracking device 356.

During use of the navigation system 10, such as when the user 200 is moving an instrument 316 relative to the subject 20, the tracking device 356 may sense the field generated by the TCA 254. As discussed above the sensed field may be used to determine a position of the instrument 316, such as a position of the working end 400, relative to the subject 20. In various embodiments, the DRF 30 may be used in combination with the tracking device 356 to determine the relative position of the instrument 316 relative to the subject 20. Accordingly, as discussed above, the icon 20i may be illustrated on the display device 39 to illustrate the position of the instrument 316 relative to the subject 20.

In having the tracking members 460-464 positioned at the respective locations on the hub 420, such as orientated orthogonally to one another, a selected degrees of freedom may be determined regarding the position of the tracking device 356. For example, six degrees of freedom may be determined including a three dimensional (e.g. x,y,z location) and orientation (e.g. three degrees of freedom). It is understood, however, that less than three of the tracking members may be used with the tracking device 356. Thus, as the motor 404 powers (e.g. rotates) the shaft 401 of the instrument 316, the position of the working end 400 may be determined and illustrated as the icon 20i. During operation of the instrument 316 (e.g. rotating and resecting) and moving the instrument 316 (e.g. toward and away from a surface) tracking of the tracking device 356 occurs.

Further, the dimension or position of the working end 400 relative to the tracking device 356 may be recalibrated or determined during a procedure. For example, the user 200 may position the working end 400 relative to the DRF 30 at a selected or known position. The navigation system 10 may then calibrate or determine the position of the working end 400 relative to the tracking device 356 by determining or tracking the DRF 30 and the tracking device 356. The instrument 316 may then be connected to the handle 406, if not already connected, and the navigation may proceed without a predetermined calibration or pre-known position of the working end 400 relative to the tracking device 356.

As discussed above, the tool assembly 20 may include various features including a working end, such as a working end or tip 50, 400. The working end may be used for various purposes, such as performing a procedure on the subject 210. The working end may be associated with an instrument portion, such as the instrument portion 24, to perform the procedure. As discussed above, the instrument portion 24 may be separable or interchangeable with a portion of the tool assembly 20, such as a handle portion 22. Further, one or more tracking portions or devices may be associated with the tool assembly 20, according to various embodiments, such as the tracking device 274 and/or tracking device 456. The tracking devices 274, 456 may be associated with the instrument assembly 20. Moreover, as discussed above, the cartridge or connection member 44 may allow for connection of the instrument portion 24, tracking device 456, or other portions relative to the navigation system 250.

As discussed above, and as illustrated in FIGS. 1 and 2, the instrument 20 may have various portions including the hand piece 22 relative to which a cartridge 44 may be positioned and/or connected. The cartridge 44, in various embodiments, may be connected to the handpiece 20 for a selected procedure such as by interconnection of a connection assembly including the rail 88 extending from the hand piece 22 and the groove 90 formed by the cartridge 44. It is understood, however, that other appropriate connection portions may be provided and that the cartridge 44, as discussed above, may allow for a connection of various systems and may include various features and portions that allow for the connection of a portion of the tool assembly 20. As discussed herein, the cartridge 44 may include various features or elements, such as passages allowing for connection of irrigation or suction, such as the irrigation passage 84, and a transmitting and/or receiving antenna 124. Further, as also discussed above, the tool assembly 20, in various embodiments including the tool assembly 316, may include the tracking device 270 and/or 356 including the various tracking members 460, 462, 464. As discussed further herein, the cartridge 44, may further include connections and/or features to allow for transmission of tracking information, powering a tracking device, or other portions including and/or in addition to the portions of the cartridge 44 discussed above including the irrigation passage 84 and other features.

Figure 8:
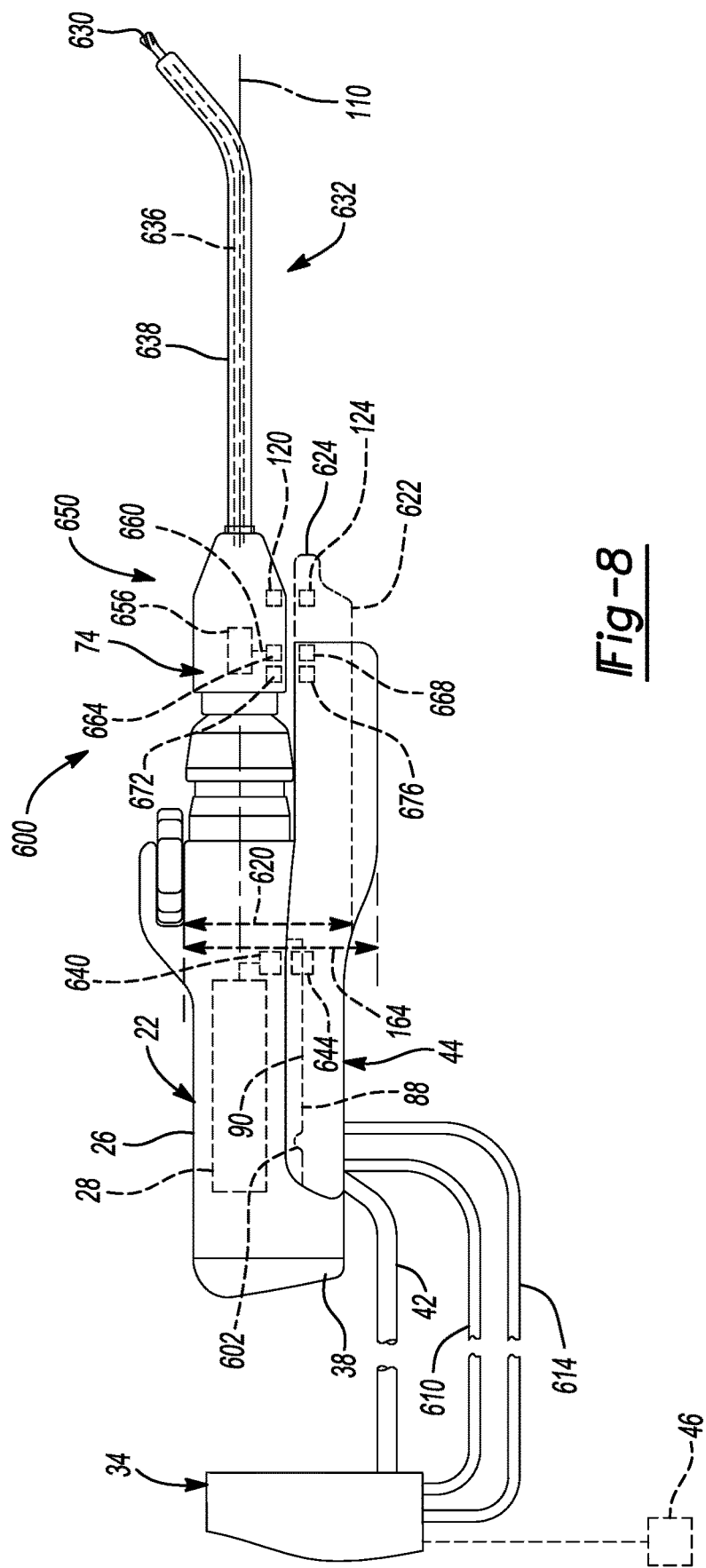
FIG. 8 is a side plan view of an instrument and connection assembly, according to various embodiments.
Figure 9:
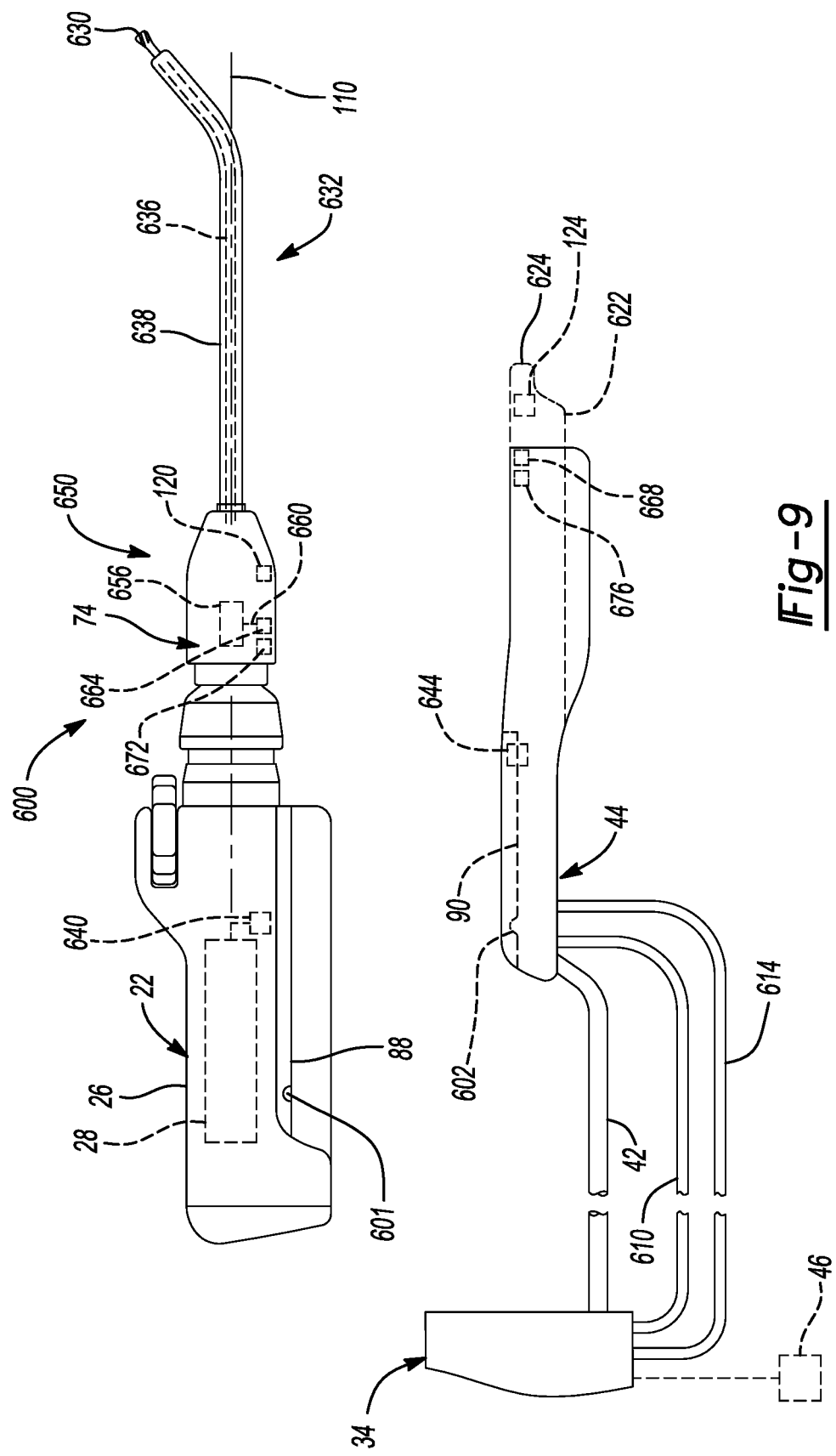
FIG. 9 is an exploded view of a tool assembly having a tool portion and a connector portion.

With continued reference to FIGS. 1-7D, and additional reference to FIG. 8 and FIG. 9, an instrument assembly 600 is illustrated. The instrument assembly 600 may include portions that are similar or identical to those discussed above. It is understood, however, that the instrument assembly 600 may include additional and/or alternative features or various combinations of the features and portions discussed above.

The instrument assembly 600 may include the cartridge 44 that has the groove 90 that engages the rail 88. Further, the cartridge 44 may include a projection or detent 601 formed relative to or within the groove 90. The detent 601 may engage a portion of the rail 44, such as an indent 602 therein, to assist in holding or locking the cartridge 44 to the handle 22. The instrument or tool assembly 600 may include the handle assembly or portion 22, as discussed above, having a housing 26 with the motor 28 therein. Also as discussed above, the motor 28 may be powered in any appropriate manner, such as through an electrical connection, hydraulic connection, or the like. As discussed above, and as illustrated in FIG. 1, an electrical connection 38 may be made substantially directly to the handle 22 including the housing 26. In various embodiments, however, an electrical connection 610 to the cartridge 44 may be present or provided from the console 34.

The electrical connection 610 may allow for electrical power to be provided to the tool assembly 600. The cartridge 44 may provide a single connection from the console 34 and/or other portions, such as the switch 46 to the tool assembly 600. The cartridge 44 may be the only connection from the handle portion 22 to external portions and/or controls, such as irrigation, suction, electrical power (or other power sources, e.g. pneumatic). The cartridge 44, as discussed above, may be selectively connected to the tool assembly 600 to provide various connections for the tool assembly 600, including power through the electrical connection 610, irrigation through the irrigation connection 42, and other connections, such as a vacuum or suction connection 614. Accordingly, the cartridge assembly 44 may provide all connections to the tool assembly 600 from the console 40. Connections may include, communication with various portions of the tool assembly 600, powering the tool assembly 600, providing irrigation and/or suction to and from the tool assembly 600, and other appropriate connections.

The cartridge 44 may generally have selected dimensions, such as the dimension 164, as discussed above that may maintain a selected dimension of the tool assembly 600, such as one substantially similar to the handle 22. It is understood, however, that the cartridge 44 may include various selected dimensions, such as a dimension 620 that is less than the dimension 164. Further the cartridge 44 may include a contoured or changing shape that includes a dimension with a tapering portion 622 near an end 624 of the cartridge 44. The end 624 may be near or adjacent a portion of the instrument portion connected to the handle 22, such as generally at or near the hub assembly 74, according to various embodiments. The cartridge 44, therefore, including the plurality of connections, such as the irrigation connection 42, the electrical connection 610, and the vacuum or suction connection 614 may include various internal portions that allow for interaction with the operation of the tool assembly 600, including a working end 630 of an instrument 632.

It is understood that the instrument 632 may be similar to the instrument 24, as discussed above according to various embodiments. Further the working end 630 may be similar the working end 50 of the instruments discussed above. The instrument 632 may have a shaft 636 that extends through a member, such as tubular member 638. The instrument 632, including the working end 630, maybe powered by the motor 28 in the handle 22.

Power may be delivered to the motor 28 via the electrical connection 610, such as through contacts, including a motor contact 640 and a cartridge motor contact 644. The cartridge motor contact 644 may be connected to the electrical line 610 such as directly via a lead, via a trace on a selected printed circuit board, or the like. The motor contact 640 may be formed in an appropriate location on the handle 22 such that placement of the cartridge 44 relative to the handle 22 allows for electrical connection between the motor contact 640 and the cartridge motor contact 644. It is further understood, however, that a selected induction or power inductive system may be provided. Accordingly, the contact 644 may be an inductive antenna that inductively provides power to the contact 640 to power the motor 28 during operation of the tool assembly 600. The connection to power the motor, may be a direct connection, such as via electrical conductive contacts, and/or a wireless power delivered may be made between the electrical connection 610 of the cartridge 44 and the motor 28.

As discussed above, the cartridge 44 may include various features and portions that allow for powering various elements of the tool assembly 600 and/or communication with various other features, such as with the navigation processing units 280 or control system 34, or other appropriate features. The tool assembly, such as the tool assembly 20, may include the ID assembly 120 associated with an instrument, such as the instrument 632 that may be removably attached to the handle assembly 22. The ID member 120 may communicate with an antenna assembly 124, which may be a transceiver, as discussed above.

The tool assembly 600 may also include other portions that are electrically powered, such as one tracking assembly or tracking device 650. The tracking device 650 may be similar to or include portions that are substantially identical to or similar to the tracking assembly 356, discussed above. In various environments, for example, the tracking device 650 may include one or more tracking members or assemblies similar to the tracking members 460, 462, 464 discussed above. As illustrated in FIG. 9, a tracking member 656 may be included with the hub 74 of the instrument assembly 632. The tracking member 656 may be substantially similar or identical to the tracking members discussed above, for example the tracking member 464. Accordingly, the tracking member 656 may include at least one microcoil, similar to the microcoil 470 and one or more leads, such as or similar to the lead 490.

A lead 660 may extend from the tracking member 656 to a power transfer pad or member 664. The power transfer pad 664 may be a contact for direct contact to a tracking device power supply pad or contact 668. The cartridge 44 may include the tracking device power pad 668 to transmit or deliver power to the tracking device 650, such as to the tracking member 656, by contact with the tracking member power pad 664 through the lead 660 to the tracking member 656. Thus, the cartridge 44 may provide power to the tracking device 650 to allow for tracking of the tool assembly 600, including the working end 630.

In various embodiments, the pad 668 may also or alternatively be an induction member, such as an antenna similar to the antenna 124. Further, in various embodiments, the antenna 124 may provide power to both the tracking device 650 and the ID member 120. Whether the same antenna or different antennas, the tracking device power pad 664 may also be receiving antenna. A current may be induced in the power pad 664 to power the tracking device 650 during operation of the tool assembly 600. It is understood that various appropriate power storage assemblies may be included with the tracking device 650 such as batteries, selected capacitive devices, or other appropriate energy storage devices. It is understood, however, that the power for the tracking device 650 may be provided substantially simultaneously and only during operation and use of the tracking device 650. Nevertheless, the power for the tracking device 650 may be provided within the cartridge 44 it is removably connected to the handle assembly 22.

The tracking device 650 may also generate a signal regarding sensed fields and/or transmitted fields. The tracking device 650 may include electromagnetic (EM) portions, including the microcoil. The EM tracking system may include or provide to wireless transmission of a tracking signal. The EM tracking system may include the TCA 254, also referred to as a localizer, and the various tracking devices can communicate through the controller 34. The controller 34 can include various amplifiers, filters, electrical isolation, and other systems. The controller 34 can also control the cons of the localizer 254 to either emit or receive an EM field for tracking. A wireless communications channel, however, such as that disclosed in U.S. Pat. No. 6,474,341, entitled "Surgical Communication Power System," issued Nov. 5, 2002, herein incorporated by reference, can be used as opposed to being coupled directly to the EM controller 34.

The tracking device 650 may also or alternatively include a direct transmission assembly 672 to transmit the signal. The transmission assembly 672 may include a conductor or a series of conductors, such as conductive pins or wires, which may directly contact receiving pins or wires in the cartridge 44. Accordingly, the tracking signal may be generated with the tracking device 650 and transmitted through the transmission assembly 672 to be received by the receiving assembly 676 in the cartridge 44. The transmission may be a transmission or physical connection, such as a conductive connection between the transmitter 672 and the receiver 676.

Alternatively, or in addition thereto, the signal may be transmitted wirelessly, as noted above, and the wireless transmission may occur in the transmission assembly 672 having an antenna assembly. Similarly, the receiver 676 may be an antenna assembly member that receives the signal from the transmitter 672. Again, the antenna for the receiver 676 may be incorporated into a single antenna that may include the inductive powering antenna 124 that may also include the tracking device power pad 668. Accordingly, according to various embodiments, the cartridge 44 may include a single antenna, such as the antenna 124, that is able to power both the ID 120 and the tracking device 650 and receive information from the ID 120 and the tracking device 650.

Thus, the cartridge 44 may allow for wireless power and information transfer, such as through a signal, from the ID 120 and the tracking device 650 for transmission to the console 34, or other appropriate portions. The cartridge 44 allows for connection of the tool assembly 600 to the console 34 substantially independently or allowing for the only connection from the tool assembly 600 to the console 34. Thus, the tool assembly 600 may be removed from the cartridge 44 and interchanged with other tool assemblies and/or moved to another procedure and cleaning and proper preparation, or for other purposes. Nevertheless, the connection of the tool assembly 600 may be performed with a single connection of the cartridge 44 to the handle 22 which may provide all appropriate and required connections such as electrical power and/or transmission of information, irrigation, suction, and other appropriate connections.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for connecting a tool assembly, comprising:
 a handpiece, including:
  a housing that is sized and shaped to be held by a hand of a user;
  a motor within the housing;
  a handpiece connector;
 a cartridge member having:
  a cartridge connector configured to engage the handpiece connector;
  a first line extending from the cartridge member and operable to be connected to a console;
  a second line extending from the cartridge member and operable to be connected to the console;
 wherein the cartridge member is configured to be removably connected to the handpiece to connect the first line and the second line to the handpiece;
 wherein at least the first line or the second line is an electrical power line;
 wherein the cartridge member further includes an electrical connector;
 wherein the electrical connector is operable to deliver electrical energy from the electrical power line to at least one of the handpiece or an instrument assembly connected to the handpiece;
 wherein the electrical connector includes an antenna operable to wirelessly transfer power to at least one of the handpiece or the instrument assembly connected to the handpiece.

2. The system of claim 1, wherein the engagement of the cartridge connector to the handpiece connector is operable to hold the cartridge member relative to the handpiece.

3. The system of claim 1, further comprising:
 the console, wherein the console is operable to provide operation features to the handpiece.

4. The system of claim 3, wherein the first line is an irrigation line wherein an irrigation fluid is able to flow from an irrigation source through the irrigation line to an irrigation passage within the handpiece after the cartridge member is operably engaged with the handpiece.

5. A system for connecting a tool assembly, comprising:
a handpiece, including:
  a housing that is sized and shaped to be held by a hand of a user;
  a motor within the housing;
  a handpiece connector;
a cartridge member having:
  a cartridge connector configured to engage the handpiece connector;
  a first line extending from the cartridge member and operable to be connected to a console;
  a second line extending from the cartridge member and operable to be connected to the console;
wherein the cartridge member is configured to be removably connected to the handpiece to connect the first line and the second line to the handpiece;
wherein the first line is at least one of an irrigation line or a suction line;
wherein the second line is an electrical power line;
a first instrument assembly operable to be removably connected to the handpiece; and
a second instrument assembly operable to be removably connected to the handpiece separate from the first instrument assembly;
wherein the first instrument assembly is configured to be connected to the handpiece and in fluid communication with an irrigation source and a power source through the cartridge member;
wherein the second instrument assembly is configured to be connected to the handpiece and in fluid communication with the irrigation source and the power source through the cartridge member;
wherein the first instrument assembly is configured to be removed from the handpiece while the cartridge member remains connected to the handpiece and the second instrument assembly is connected to the handpiece while the cartridge member remains connected to the handpiece.

6. The system of claim 5, wherein the first line is the suction line.

7. The system of claim 5, wherein the cartridge member further includes an electrical connector;
wherein the electrical connector is operable to deliver electrical energy from the electrical power line to at least one of the handpiece, the first instrument assembly or the second instrument assembly connected to the handpiece.

8. The system of claim 7, wherein the electrical connector includes an antenna operable to wirelessly transfer power to at least one of the handpiece, the first instrument assembly or the second instrument assembly connected to the handpiece.

9. The system of claim 5, wherein the cartridge member further includes a receiver assembly;
wherein the receiver assembly is operable to receive a signal from at least one of an identification member associated with an instrument connected to the handpiece or a tracking device associated with the instrument connected to the handpiece.

10. The system of claim 9, wherein the receiver assembly includes an antenna to wirelessly receive the signal from at least one of the identification member associated with the instrument connected to the handpiece and the tracking device associated with the instrument connected to the handpiece.

11. The system of claim 5, wherein the cartridge member provides an only connection to the console from the handpiece and the first instrument assembly or the second instrument assembly.

12. The system of claim 11, further comprising:
a first identification member and a first tracking device associated with the first instrument assembly;
a second identification member and a second tracking device associated with the second instrument assembly;
an antenna within the cartridge member configured to:
  interrogate the first identification member and the second identification member and transmit a signal based on the interrogation; and
  receive a tracking signal from the first tracking device and the second tracking device.

13. A system for connecting a tool assembly, comprising:
a handpiece, including:
  a housing that is sized and shaped to be held by a hand of a user;
  a motor within the housing;
  a handpiece connector;
a cartridge member having:
  a cartridge connector configured to engage the handpiece connector;
  a first line extending from the cartridge member and operable to be connected to a console;
  a second line extending from the cartridge member and operable to be connected to the console;
a first instrument assembly configured to be removably connected to the handpiece to be powered by the motor;
a first tracking device associated with the first instrument assembly configured to be connected to a surgical navigation system via the first line; and
an irrigation system connected to the second line;
wherein the cartridge member is configured to be removably connected to the handpiece to connect the first line and the second line to the handpiece.

14. The system of claim 13, further comprising:
the surgical navigation system configured to track the first tracking device based on a signal from the first tracking device via the first line;
wherein the first line is further configured to deliver power to the tracking device.

15. The system of claim 14, further comprising:
a second instrument assembly configured to be removably connected to the handpiece to be powered by the motor; and
a second tracking device associated with the second instrument assembly configured to be connected to the surgical navigation system via the first line;
wherein the first instrument assembly is configured to be removed from the handpiece while the cartridge member remains connected to the handpiece and the second instrument assembly is connected to the handpiece while the cartridge member remains connected to the handpiece.

16. The system of claim 15, wherein the cartridge member is an only connection to the console from the handpiece.

17. A system for connecting a tool assembly, comprising:
a handpiece, including:
  a housing that is sized and shaped to be held by a hand of a user;
  a motor within the housing;
  a first connector configured to engage an instrument assembly for performing a procedure with at least a portion of the instrument assembly;
  a second connector formed on the housing;

a cartridge member having a cartridge connector configured to engage and hold the cartridge member relative to the handpiece;
wherein the cartridge member is configured to be removably connected to the handpiece to connect a line to the handpiece;
wherein the second connector includes a rail;
wherein the cartridge connector includes a groove;
wherein the rail has an exterior dimension that is received in the groove to connect the cartridge member to the handpiece;
wherein the cartridge member further includes a receiver assembly;
wherein the receiver assembly is operable to receive a signal from at least one of an identification member associated with an instrument connected to the handpiece or a tracking device associated with the instrument connected to the handpiece;
wherein the receiver assembly includes an antenna to wirelessly receive the signal from at least one of the identification member associated with the instrument connected to the handpiece and the tracking device associated with the instrument connected to the handpiece.

18. The system of claim 17, wherein the line comprises an irrigation tube;
wherein the instrument assembly includes an irrigation passage;
wherein the cartridge member includes an irrigation outlet;
wherein an irrigation fluid is able to flow from an irrigation source through the irrigation passage of the instrument assembly after the cartridge is connected to the handpiece.

19. The system of claim 18, wherein the cartridge member is fixedly connected to the irrigation tube.

20. A system for connecting a tool assembly, comprising:
a handpiece, including:
a housing that is seized and shaped to be held by a hand of a user;
a motor within the housing;
a first connector configured to engage an instrument assembly for performing a procedure with at least a portion of the instrument assembly;
a second connector formed on the housing;
a cartridge member having a cartridge connector to engage and hold the cartridge member relative to the handpiece; and
an instrument assembly, wherein the instrument assembly includes a first instrument assembly and a second instrument assembly;
wherein the cartridge member is configured to be removably connected to the handpiece to connect a line to the handpiece;
wherein the first instrument assembly is configured to be connected to the handpiece and in fluid communication with an irrigation source through the cartridge member;
wherein the second instrument assembly is configured to be connected to the handpiece and in fluid communication with the irrigation source through the cartridge member;
wherein the first instrument assembly is configured to be removed from the handpiece while the cartridge member is connected to the handpiece and the second instrument assembly is connected to the handpiece while the cartridge member is connected to the handpiece.

21. The system of claim 20, further comprising:
a first identification member associated with the first instrument assembly;
a second identification member associated with the second instrument assembly;
an antenna within the cartridge member to interrogate the first identification member and the second identification member and transmit a signal based on the interrogation;
wherein the signal is configured to allow determination of an identify of either the first instrument assembly or the second instrument assembly.

22. A system for connecting a tool assembly, comprising:
a handpiece, including:
a housing that is sized and shaped to be held by a hand of a user;
a motor within the housing;
a first connector configured to engage an instrument assembly for performing a procedure with at least a portion of the instrument assembly;
a second connector formed on the housing;
a cartridge member having a cartridge connector configured to engage and hold the cartridge member relative to the handpiece;
wherein the cartridge member is configured to be removably connected to the handpiece to connect a line to the handpiece;
wherein the cartridge member further includes a control member configured to receive an input from a user to change an operation of at least one of the motor, a flow from an irrigation source, or combinations thereof;
a first identification member and a first tracking device associated with a first instrument assembly;
a second identification member and a second tracking device associated with a second instrument assembly;
an antenna within the cartridge member configured to:
interrogate the first identification member and the second identification member and transmit a signal based on the interrogation; and
receive a tracking signal from the first tracking device and the second tracking device.

23. A system for connecting a tool assembly, comprising:
a handpiece, including:
a housing that is sized and shaped to be held by a hand of a user;
a motor within the housing;
a first connector configured to engage an instrument assembly for performing a procedure with at least a portion of the instrument assembly;
a second connector formed on the housing;
a cartridge member having a cartridge connector configured to engage and hold the cartridge member relative to the handpiece;
wherein the cartridge member is configured to be removably connected to the handpiece to connect a line to the handpiece;
wherein the cartridge member further includes an indicator configured to provide an output to indicate a current operation of at least one of the motor, a flow from an irrigation source, or combinations thereof;
a first instrument assembly operable to be removably connected to the handpiece; and
a second instrument assembly operable to be removably connected to the handpiece separate from the first instrument assembly;

wherein the first instrument assembly is configured to be connected to the handpiece and in fluid communication with an irrigation source and a power source through the cartridge member;

wherein the second instrument assembly is configured to be connected to the handpiece and in fluid communication with the irrigation source and the power source through the cartridge member;

wherein the first instrument assembly is configured to be removed from the handpiece while the cartridge member remains connected to the handpiece and the second instrument assembly is connected to the handpiece while the cartridge member remains connected to the handpiece.

* * * * *

UNITED STATES PATENT AND TRADEMARK OFFICE
CERTIFICATE OF CORRECTION

PATENT NO. : 11,389,184 B2
APPLICATION NO. : 16/055782
DATED : July 19, 2022
INVENTOR(S) : Jeffrey M. Schwamb et al.

It is certified that error appears in the above-identified patent and that said Letters Patent is hereby corrected as shown below:

In the Specification

Column 3, Line 6, delete "20." and insert --26-- therefor

Column 3, Line 49, delete "24" and insert --22-- therefor

Column 4, Line 4, delete "24" and insert --76-- therefor

Column 4, Line 8, delete "82" and insert --84-- therefor

Column 4, Line 42, delete "44" and insert --84-- therefor

Column 5, Line 37, delete "94." and insert --100.-- therefor

Column 5, Line 49, delete "42" and insert --84-- therefor

Column 7, Line 41, delete "electronics" and insert --electrical-- therefor

Column 9, Line 8, delete "54." and insert --50.-- therefor

Column 10, Line 21, delete "44" and insert --24-- therefor

Column 12, Line 2, delete "38," and insert --264,-- therefor

Column 18, Line 40, delete "20" and insert --22-- therefor

Column 18, Line 54, delete "316," and insert --20,-- therefor

Signed and Sealed this
Fourth Day of October, 2022

*Katherine Kelly Vidal*

Katherine Kelly Vidal
*Director of the United States Patent and Trademark Office*

Column 19, Line 36, delete "40." and insert --34.-- therefor

Column 21, Line 19, delete "cons" and insert --coils-- therefor